United States Patent [19]

Skuballa et al.

[11] 4,088,775
[45] May 9, 1978

[54] 15-ETHYLENEDIOXY-PROSTANOIC ACID DERIVATIVES AND ESTERS THEREOF AND INTERMEDIATES THEREOF

[75] Inventors: Werner Skuballa; Bernd Raduchel; Helmut Vorbruggen; Walter Elger; Wolfgang Losert; Olaf Loge, all of Berlin, Germany

[73] Assignee: Schering Aktiengesellschaft, Berlin and Bergkamen, Germany

[21] Appl. No.: 595,015

[22] Filed: Jul. 11, 1975

[30] Foreign Application Priority Data
Jul. 12, 1974 Germany .................... 2434133

[51] Int. Cl.² .............. A61K 31/335; A61K 31/36; C07D 317/00
[52] U.S. Cl. ................ 424/278; 260/340.9 P; 424/282; 542/429; 542/430
[58] Field of Search .......... 260/340.9 P; 424/278, 424/279; 542/429, 430

[56] References Cited

U.S. PATENT DOCUMENTS

| 3,900,512 | 8/1975 | Sih .................... 260/340.9 P |
| 3,962,218 | 6/1976 | Raduchel et al. ...... 260/240 R |

Primary Examiner—Sam Rosen
Attorney, Agent, or Firm—Millen & White

[57] ABSTRACT

Prostanoic acid derivatives of the formula

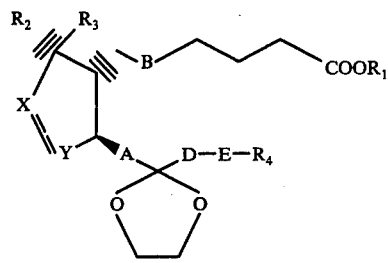

wherein $R_1$ is a hydrogen atom, alkyl of 1–10 carbon atoms, aryl or —$CH_2$—U—V wherein U is a direct bond, carbonyl, or carbonyloxy and V is phenyl or substituted phenyl, e.g. substituted by at least one of phenyl, alkoxy of 1–2 carbon atoms or a halogen atom; one of $R_2$ and $R_3$ is hydroxy and the other is a hydrogen atom or $R_2$ and $R_3$ collectively are an oxygen atom; A is —$CH_2$—$CH_2$— or trans—CH=CH; B is —$CH_2$—$CH_2$— or cis—CH=CH; D and E collectively are a direct bond, or D is alkylene or 1–5 carbon atoms and E is an oxygen or sulfur atom; $R_4$ is alkyl of 1–10 carbon atoms, alkyl of 1–5 carbon atoms substituted by unsubstituted or substituted aryl, unsubstituted or substituted aryl, or benzodioxol-2-yl-; X—Y is

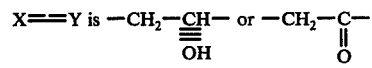

when one of $R_2$ and $R_3$ is a hydroxy group and the other is a hydrogen atom or X—Y is

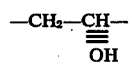

or —CH=CH— when $R_2$ and $R_3$ collectively are an oxygen atom; and when $R_1$ is a hydrogen atom, the physiologically acceptable salts thereof with bases, have an activity spectrum similar to but stronger and longer lasting activity than the corresponding natural prostaglandins.

90 Claims, No Drawings

15-ETHYLENEDIOXY-PROSTANOIC ACID DERIVATIVES AND ESTERS THEREOF AND INTERMEDIATES THEREOF

BACKGROUND OF THE INVENTION

This invention relates to novel prostanoic acid derivatives, processes for the preparation and use thereof, and to novel intermediates produced in these processes.

Prostaglandins are C-20-unsaturated fatty acids showing a variety of physiological effects (T. O. Oesterling et al., J. Pharmaceutical Sciences 61 [1972] 1861–1895). Such effects are, for example, vasodilation, bronchodilatation, inhibition of the stomach acid secretion, suppression of the aggregation of blood platelets. Various natural prostaglandins, such as, for example, prostaglandin $E_2$ and prostaglandin $F_{2\alpha}$, are suitable for triggering menstruation, for including abortions and for the induction of labor.

The conventional prostaglandins are derivatives of prostanoic acid having the following formula:

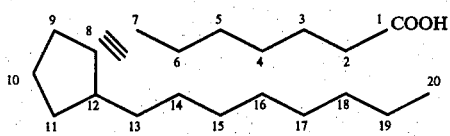

Examples of known prostaglandins, called PG hereinbelow, are:

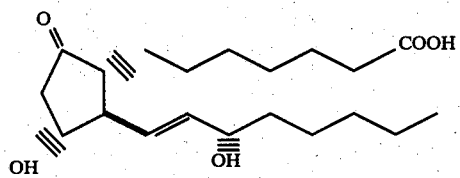

PG $E_1$

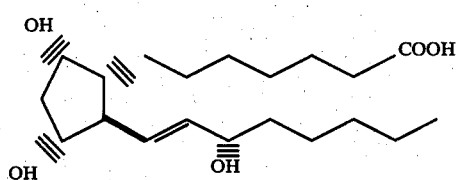

PG $F_{1\alpha}$

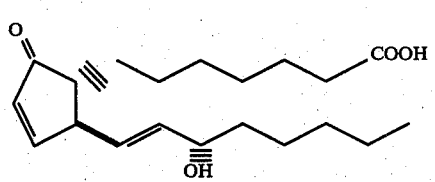

PG $A_1$

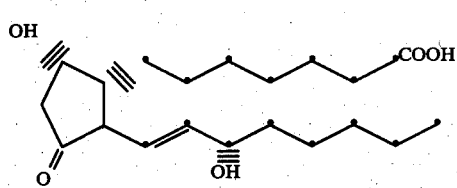

PG $D_1$

PG $E_2$, PG $F_{2\alpha}$, PG $A_2$, PG $D_2$ are in conformance with the compounds of the PG′$_1$ series with respect to their basic structure but linking of the C-5 and C-6 atoms is different. In the PG′$_2$ series, the C-5 and C-6 carbon atoms are linked by a cis-double bond. PG $F_{2\alpha}$ has the formula:

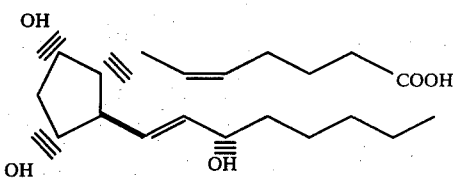

PG $E_3$, PG $F_{3\alpha}$, and PG $A_3$ differ from the corresponding PG′$_2$ compounds in that the C-17 and C-18 atoms are linked by a cis-double bond.

PG $F_{3\alpha}$ has the formula:

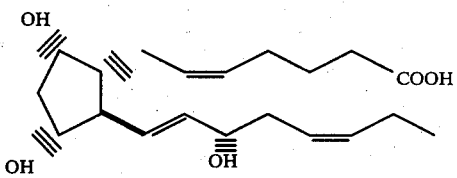

It is generally known that the physiological effects of the prostaglandins are only of short duration in the mammalian organism as well as in vitro, since they are rapidly converted into pharmacologically inactive metabolic products. Thus, a physiologically inactive metabolite is formed by oxidation of the allylic hydroxy function on the C-15 atom due to 15-hydroxyprostaglandin dehydrogenases. From PG $F_{2\alpha}$, for example, the following 13,14-dihydro-15-dehydro derivative is formed by this oxidation as well as by a hydrogenation step, as the main metabolite (E. Granstroem and B. Samuelson, Eur. J. Biochem. 10 [1969] 411):

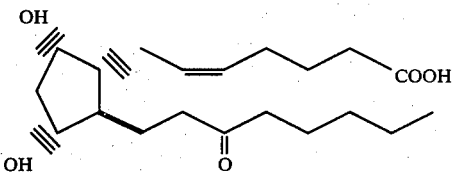

which possesses the physiological effects typical for this class of compounds only to a very greatly diminished extent.

Therefore, it has been desired to develop prostaglandin analogs having an activity spectrum comparable to that of the natural prostaglandins and to make structural changes by means of which the duration and selectivity of effectiveness are increased.

In U.S. Application Ser. No. 472,738, filed May 23, 1974, ketals of natural 15-dehydroprostaglandins are described. It has now been found that, by modifying the lower prostaglandin side chain while retaining the ketal structure element, substantially increased physiological effects are being evoked.

The novel ketals surpass in their activity the natural prostaglandins. Furthermore, the effectiveness lasts over a longer period of time. The 15-ketoprostaglandins corresponding to these ketals show the physiological effects typical for prostaglandins only in greatly weakened form. Therefore, the advantageous properties of the novel compounds could not be expected. The novel compounds moreover have the advantage that they are very readily accessible, do not have a center of asymmetry on the C-15 atom, and thus can be obtained in the pure form without any great technical expenditure.

SUMMARY OF THE INVENTION

In a composition aspect, this invention relates to prostanoic acid derivatives of the general Formula I

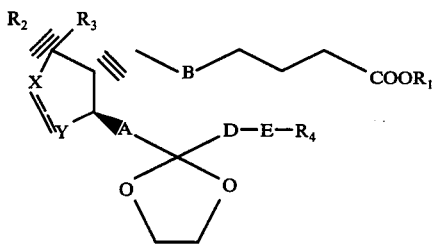

wherein $R_1$ is a hydrogen atom, straight-chain or branched alkyl of 1-10 carbon atoms, a substituted or unsubstituted aryl, or —$CH_2$—U—V wherein U is a direct bond, carbonyl, or carbonyloxy, and V is phenyl or substituted phenyl, e.g. substituted by one or more of phenyl alkoxy of 1-2 carbon atoms, or halogen, preferably bromine; one of $R_2$ and $R_3$ is hydroxy and the other is a hydrogen atom or $R_2$ and $R_3$ collectively are an oxygen atom; A is —$CH_2$—$CH_2$— or trans-CH=CH; B is —$CH_2$—$CH_2$— or cis—CH=CH—; D and E collectively are a direct bond or D is straight-chain or branched alkylene of 1-5 carbon atoms and E is an oxygen or sulfur atom; $R_4$ is straight-chain or branched alkyl of 1-10 carbon atoms, straight-chain or branched alkyl of 1-5 carbon atoms substituted by aryl, benzodioxol-2-yl- or aryl, X—Y is

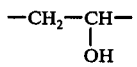

or when one of $R_2$ and $R_3$ is hydroxy and the other is a hydrogen atom,

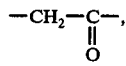

or when $R_2$ and $R_3$ collectively are an oxygen atom —CH=CH—; and when $R_1$ is a hydrogen atom, the physiologically acceptable salts thereof with bases, including the corresponding antipodes and racemates of General Formula I.

In another composition aspect, this invention relates to pharmaceutical compositions comprising one or more compounds of Formula I or, when $R_1$ is a hydrogen atom, a physiologically acceptable salt thereof with a base, in admixture with a pharmaceutically acceptable carrier.

In a further composition aspect, this invention relates to novel intermediates useful for the production of compounds of Formula I and, when $R_1$ is a hydrogen atom, salts thereof with a base.

In process aspects, this invention relates to processes for the production of the novel compounds of this invention and to methods for their use.

DETAILED DISCUSSION

Examples of $R_1$ alkyl groups of 1-10 carbon atoms are methyl, ethyl, propyl, isopropyl, n-butyl, sec.-butyl, n-pentyl, n-hexyl, n-octyl and n-nonyl.

Examples of substituted phenyl V groups are p-diphenyl, p-chlorophenyl, p'-chloro-p-diphenyl, p-alkoxyphenyl wherein alkoxy is of 1-4 carbon atoms, and m,m'-dimethylphenyl.

Examples of alkylene D groups are methylene, ethylene, α-propylene, β-propylene, trimethylene, tetramethylene, β-butylene.

Examples of substituted or unsubstituted aryl $R_1$ and $R_4$ groups are phenyl, 1-naphthyl and 2-naphthyl, each of which can be substituted by 1-3 halogen atoms, 1 phenyl group, 1-3 alkyl groups of respectively 1-4 carbon atoms, 1 chloromethyl, fluoromethyl, trifluoromethyl, carboxyl or hydroxy group.

Examples of contemplated classes of compounds within the scope of Formula I are those wherein:

(a) one only of A and B is —CH=CH—, preferably B;
(b) both of A and B are —CH=CH—;
(c) $R_2$ and $R_3$ are an oxygen atom, including those of (a) and (b);
(d) one of $R_2$ and $R_3$ is a hydroxy group, preferably $R_2$, including those of (a) and (b);
(e) X—Y is

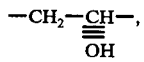

including those of (a), (b), (c) and (d);
(f) X—Y is

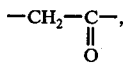

including those of (a) and (b);
(g) X—Y is —CH=$CH_2$, including those of (a) and (b);
(h) $R_1$ is H, including those of each of (a) – (g), inclusive;
(i) the salts with bases of the compounds of (h), preferably an alkali metal or amine salt;
(j) $R_1$ is alkyl of 1-4 carbon atoms, preferably methyl, including each of (a) – (g), inclusive;
(k) $R_1$ is —$CH_2$—U—V as defined above, preferably p-phenylphenacyl, p-Cl-phenyl, p-F-phenyl or p-phenylphenyl, including each of (a) – (g), inclusive;
(l) D is alkylene, preferably methylene, E is 0 or S, preferably 0, and $R_4$ is alkyl of 1-4 carbon atoms, preferably methyl or n-propyl, phenyl, p-substituted phenyl, preferably p-Cl- or p-F-phenyl, m-substituted phenyl, preferably m-$CF_3$-phenyl, or naphthyl, preferably 2-naphthyl, including each of (a) – (k), inclusive;
(m) D and E are a direct bond and $R_4$ is alkyl, preferably straight chain, e.g., n-butyl and n-heptyl, substituted phenyl, preferably p-substituted phenyl, e.g., p-phenylphenyl, p-Cl-phenyl or phenalkyl, e.g., phenethyl, including each of (a) – (k), inclusive.

For the salt formation, the following can, for example, be used as physiologically compatible bases: alkali hydroxides, such as sodium or potassium hydroxide, alkaline earth hydroxides, such as calcium hydroxide, ammonia, amines, such as ethanolamine, diethanolamine, triethylamine, N-methylglucamine, morpholine, tris(hydroxymethyl)methylamine.

The invention furthermore relates to a process for the preparation of the novel prostaglandins of general Formula I, wherein (a) a ketone of general Formula II

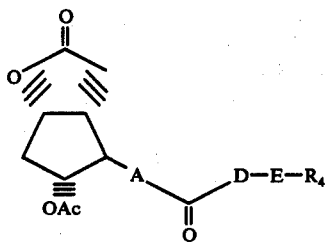
(II)

wherein A, D, E and R₄ have the values given for Formula I and Ac represents an aliphatic or aromatic acyl group, is ketalized with ethylene glycol;

the thus-obtained ketal of general Formula II

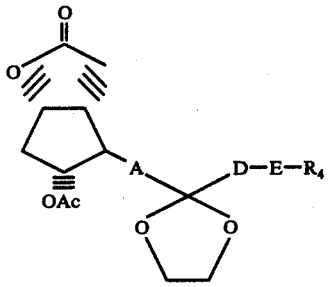
(III)

wherein A, D, E and R₄ have the values given for Formula I and Ac has the values given for Formula II is reduced in accordance with a simplified Corey synthesis as described in U.S. Patent Application Ser. No. 472,737, whose disclosure is incorporated by reference, with diisobutylaluminum hydride to the hemiacetal of general Formula IV

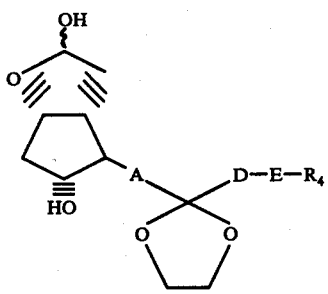
(IV);

and the hemiacetal of general Formula IV is reacted with a Wittig reagent of the general Formula V

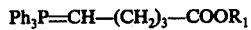
(V)

wherein Ph represents a phenyl group and $R_1$ has the values given for Formula I to compounds of general Formula Ia

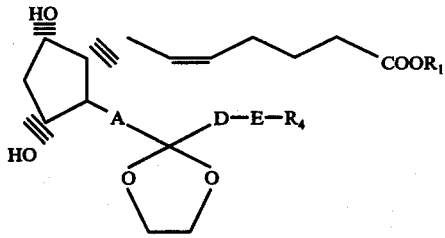
(Ia);

and, depending on the finally desired values of $R_1$, $R_2$, and $R_3$ and B in the final product of general Formula I, optionally, in the thus-obtained compounds, in any desired succession, a 1-carboxy-group is esterified and/or the 9-OH-group and/or the 11-OH-group is oxidized, and optionally thereafter a dehydration is carried out while eliminating the 11-hydroxy-group, or the 9-keto-group is reduced, and the 9β-OH-compound is isolated and/or the 5,6-double bond is hydrogenated, and optionally the 1-carboxy compounds are converted into the salts thereof with physiologically compatible bases; or (b) a ketal of general Formula III prepared according to process (a) wherein A is a trans-double bond, D is a CH₂-group, E is an oxygen atom, R₄ is a substituted or unsubstituted aryl residue, and Ac has the values given for Formula II is converted by interesterification into an alcohol of the general Formula VI

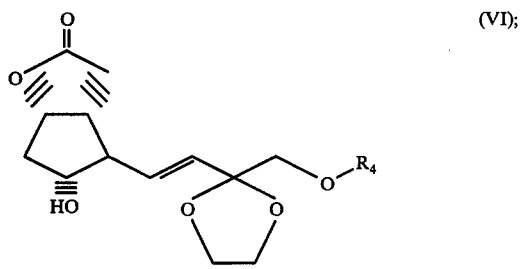
(VI);

the tetrahydropyranyl ether of general Formula VII is produced therefrom by reaction with dihydropyran

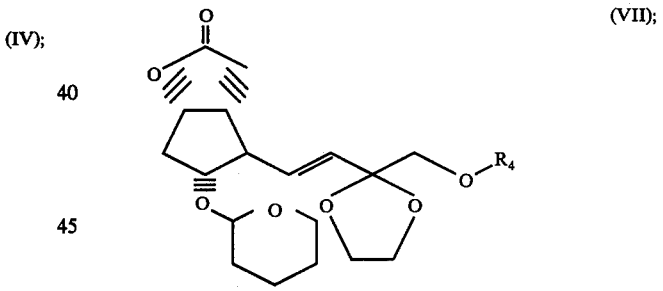
(VII);

and this compound is thereafter reduced with diisobutylaluminum hydride to the hemiacetal of general Formula VIII

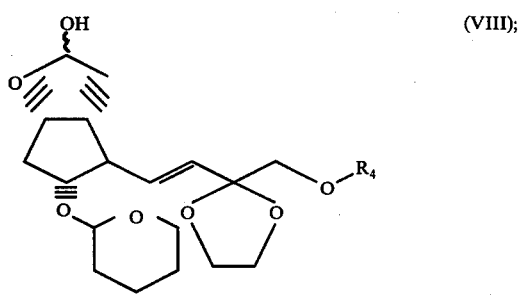
(VIII);

and the hemiacetal of general Formula VIII is reacted with a Wittig reagent of general Formula V to compounds of general Formula IX

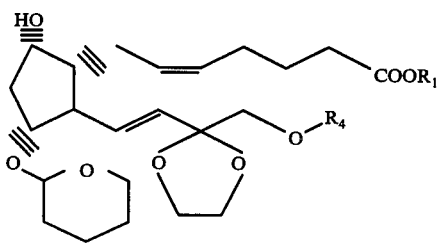

(IX);

and, depending on the finally desired values of $R_1$, $R_2$, $R_3$ in Formula I, the tetrahydropyranyl ether residue is split off or is oxidized with Jones reagent to compounds of general Formula X

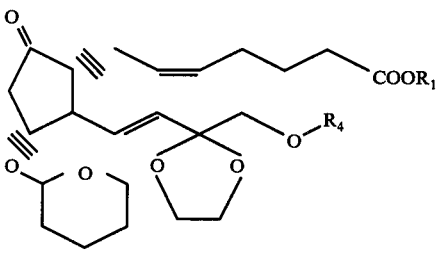

(X);

and subsequently the tetrahydropyranyl ether is split, the carboxy group is esterified, or the 9-keto-group is reduced and the 9β-OH-compound is isolated.

In Formulae II and III, Ac is the acyl radical of an aliphatic or aromatic carboxylic acid. Examples of radicals of aliphatic carboxylic acids are acetyl, propionyl, butyryl, valeryl, hexanoyl and heptanoyl. However, also possible are acyl radicals of aliphatic carboxylic acids which are long-chain, branched and substituted by halogen, amino or hydroxy. Suitable radicals of aromatic carboxylic acids are, e.g., benzoyl, p-toluyl, p-nitrobenzoyl, p-phenylbenzoyl, etc.

It is, of course, also possible to use, in place of the aforementioned, optically active compounds, also the corresponding antipodes thereof or the racemates.

For the ketalization according to method (a), a ketone of general Formula II is conventionally ketalized. Thus, the ketone is heated with ethylene glycol in the presence of an acidic catalyst while splitting off water. Especially suitable as the acidic catalysts are p-toluenesulfonic acid and perchloric acid.

The ketals of general Formula III obtained in the first stage can be reduced with a solution of diisobutylaluminum hydride in an inert solvent to the hemiacetals of general Formula IV at low temperatures. During this step, the ester group on the cyclopentane ring is cleaved.

The reaction is conducted at low temperatures, preferably at temperatures of about −120° to −30° C. in an inert solvent, such as hexane, toluene, glyme, diethyl ether, or tetrahydrofuran.

The hemiacetal of general Formula IV is reacted with the Wittig reagent of general Formula V produced from the corresponding phosphonium bromide with methanesulfinylmethylsodium or potassium tert.-butylate in dimethyl sulfoxide. The reaction is conducted at temperatures of 0°–100° C., preferably 20°–80° C., in an aprotic solvent, such as dimethyl sulfoxide or dimethylformamide. The Wittig reagent can also be liberated during the reaction from 4-$R_1$-O-CO-triphenylbutylphosphonium bromide with potassium tert.-butylate.

The selective oxidation of the 9-hydroxy-group can be accomplished with silver carbonate, "Fetizon" reagent (Tetrahedron 29, 2867 [1973]), active manganese dioxide (Proc.Chem.Soc. 1964, 110), or platinum with oxygen (Adv. in Carbohydrate Chem. 17, 169 [1962]) in an inert solvent. Suitable solvents are benzene, toluene, xylene, ethyl acetate, acetone, tetrahydrofuran, diethyl ether, and dioxane. The reaction temperatures range between 20° and 110° C. during the silver carbonate or "Fetizon" oxidation, and preferably at the boiling temperature of benzene or toluene; when oxidizing with manganese dioxide or platinum/oxygen, the temperatures are preferably 20°–50° C.

The oxidation of the 11-hydroxy-group can be conducted with Jones reagent (J. Chem. Soc. 1953, 2555) at −40° to +20° C., preferably at −20° C.

The ketals of general Formula III prepared according to method (a) are interesterified to compounds of general Formula VI with an alkali carbonate, e.g., potassium carbonate, in methanol at 0°–50° C., preferably at 25° C. The thus-obtained alcohol is converted into the tetrahydropyranyl ether of general Formula VII with dihydropyran and an acidic catalyst, preferably p-toluenesulfonic acid, in an inert solvent, preferably methylene chloride, at temperatures of between 0° and 50° C., preferably between 5° and 20° C. By reduction with a solution of diisobutylaluminum hydride or lithium tri-tert.-butoxyaluminum hydride in an inert solvent, the hemiacetals of general Formula VIII are obtained. The reaction is carried out at low temperatures, preferably at about −120° to −30° C. in an inert solvent, such as hexane, toluene, glyme, diethyl ether, or tetrahydrofuran. The hemiacetal of general Formula VIII is reacted to compounds of general Formula IX with the Wittig reagent of general Formula V obtained from the corresponding phosphonium bromide with methanesulfinylmethylsodium or potassium tert.-butylate in dimethyl sulfoxide. The reaction is conducted at temperatures of 0°–100° C., preferably 20°–80° C. in an aprotic solvent, such as dimethyl sulfoxide or dimethylformamide. The Wittig reagent can also be liberated during the reaction from 4-$R_1$-O-CO-triphenylbutylphosphonium bromide with potassium tert.-butylate.

The oxidation of the 9-hydroxy-group to the ketone of general Formula X is accomplished with Jones reagent (J. Chem. Soc. 1953, 2555). The reaction is carried out with an excess of the oxidizing agent in a suitable diluent, such as acetone, at temperatures of between 0° and −50° C., preferably at −20° C. The reaction is generally terminated after 5–30 minutes.

The hydrolysis of the compounds of general Formulae IX and X to the compounds of general Formula I wherein $R_1$, $R_2$, and $R_3$ have the values given for Formula I and A is a trans-double bond, B a cis-double bond, D a $CH_2$-group, E an oxygen atom, $R_4$ a substituted or unsubstituted aryl residue, and X≡Y stands for

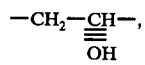

is effected according to conventional methods in an aqueous solution of an organic acid, such as, for example, acetic acid, propionic acid, etc., or in an aqueous solution of an inorganic acid, e.g., hydrochloric acid. To improve solubility, a water-miscible inert organic solvent is advantageously added. Suitable organic solvents are, for example, alcohols, such as methanol or ethanol, and ethers, such as dimethoxyethane, dioxane, and tetrahydrofuran. Tetrahydrofuran is preferably utilized. The hydrolysis is conducted at temperatures of between 20° and 80° C., preferably at 25° C.

In order to prepare the corresponding $F_{2\beta}$-analogs ($R_2$ = H, $R_3$ = OH), the PGE derivatives ($R_2$ and $R_3$ = O) prepared according to method (a) or (b) are treated with a reducing agent suitable for the reduction of ketones. Suitable reducing agents are, for example, sodium borohydride or zinc borohydride. The thus-produced mixture of epimers is separated in the usual manner by column or layer chromatography.

The compounds obtained according to process (a) or (b) can optionally be conventionally esterified and/or hydrogenated thereafter. The free acids ($R_1$ = $CO_2H$) can be converted into the salts with physiologically compatible bases.

To produce the esters of general Formula I wherein $R_1$ is an alkyl group of 1-10 carbon atoms, the 1-carboxy compounds are reacted in a manner known per se with diazo hydrocarbons. The esterification with diazo hydrocarbons takes place, for example, by mixing a solution of the diazo hydrocarbon in an inert solvent, preferably in diethyl ether, with the 1-carboxy compound in the same or another inert solvent, e.g. methylene chloride. After the reaction is terminated within 1-30 minutes, the solvent is removed and the ester is purified in the usual manner.

Diazoalkanes are either known or can be produced according to known methods (Org. Reactions, 8: 389-394 [1954]).

In order to introduce the ester group —$CH_2$—U—V—for $R_1$, the 1-carboxy compound of general Formula I is reacted, in the presence of an agent splitting off hydrogen halide, with a halogen compound of the general formula

wherein
Hal is a halogen atom, preferably bromine,
U is a direct bond, a carbonyl group, or a carbonyloxy group, and
V is a phenyl ring substituted by one or more phenyl groups, alkoxy groups of 1-2 carbon atoms, or halogen atoms, preferably bromine atoms.

Examples of suitable agents for splitting hydrogen halide are silver oxide, sodium carbonate, potassium carbonate, sodium bicarbonate, potassium bicarbonate, or amines, such as trimethylamine, triethylamine, tributylamine, trioctylamine, and pyridine. The reaction with the halogen compound is conducted in an inert solvent, preferably in acetone, acetonitrile, dimethylacetamie, dimethylformamide, or dimethyl sulfoxide at temperatures of −80° to +100° C., preferably at room temperature.

For the production of the esters of general Formula I wherein $R_1$ represents a substituted or unsubstituted aryl group, the 1-carboxy compounds are reacted with the corresponding arylhydroxy compounds with dicyclohexylcarbodiimide in the presence of a suitable base, e.g., pyridine or triethylamine in an inert solvent. Suitable solvents are methylene chloride, ethylene chloride, chloroform, ethyl acetate, tetrahydrofuran, preferably chloroform. The reaction is conducted at temperatures of between −30° and +50° C., preferably at 10° C.

The hydrogenation of the 13,14- and/or 5,6-double bond is conducted conventionally in a hydrogen atmosphere in the presence of a noble metal catalyst. A suitable catalyst is, for example, 10% palladium on charcoal. If the hydrogenation is carried out at room temperature, the 5,6- as well as the 13,14-double bonds can be saturated. At low temperatures, preferably at −80° to −10° C., the cis-5,6-double bond can be hydrogenated before the trans-13,14-double bond. A selective reduction of the cis-5,6-double bond with the simultaneous presence of a trans-13,14-double bond is also effected by means of the catalyst nickel boride or tris(triphenylphosphine)rhodium(I) chloride.

The prostaglandin derivatives of general Formula I wherein $R_1$ is a hydrogen atom can be converted into salts with suitable amounts of the corresponding inorganic bases under neutralization. For example when dissolving the corresponding PG acids in water containing the stoichiometric quantity of the base, the solid inorganic salt is obtained after evaporation of the water or after adding a water-miscible solvent, e.g., alcohol or acetone.

To produce an amine salt, the PG acid is dissolved in a suitable solvent, for example ethanol, acetone, diethyl ether, or benzene, and at least the stoichiometric amount of the amine is added to this solution. During this procedure, the salt is ordinarily obtained in the solid phase.

In addition to the compounds of general Formula I the present invention also encompasses the novel intermediate products of general Formulae III through X.

The novel prostanoic acid derivatives of general Formula I are valuable pharmaceuticals, since they show, with a similar spectrum of activity, an essentially stronger and above all longer lasting effectiveness than the corresponding natural prostaglandins.

The novel prostaglandin analogs of the E, D, and F type have a very strong luteolytic effect, i.e., in order to trigger a luteolysis substantially lower doses are required than in case of the corresponding original prostaglandins.

Also for inducing abortions, substantially lower quantities of the novel prostaglandin analogs are required as compared to the original prostaglandins.

When recording the isotonic uterus contraction on narcotized rats and on the isolated rat uterus, it is found that the compounds of the present invention are substantially more effective, and their activities are longer lasting than in case of the natural prostaglandins.

The novel prostanoic acid derivatives are suitable, after a one-time intrauterine administration, for inducing menstruation or for interrupting pregnancy. The following table will demonstrate this fact, using as an example the compounds 1-12 of this invention as compared to natural PG $F_{2\alpha}$. The investigations were conducted on gravid rats according to the customary methods. Thus, pregnant rats were treated from the 4th to the 7th day of pregnancy subcutaneously with the compounds of this invention. On the 9th day, the animals were sacrificed and the uteri investigated for sites of implantation.

TABLE

| Compound Investigated | Relative Effect (PG $F_{2\alpha}$= 1) on Abort in Rats |
|---|---|
| 1 (5Z,13E)-(8R,9S,11R,12R)-9,11-Dihydroxy-15,15-ethylenedioxy-16-phenoxy-17,18,19,20-tetranor- | |

TABLE-continued

| | Compound Investigated | Relative Effect (PG $F_{2\alpha}$= 1) on Abort in Rats |
|---|---|---|
| | prostadienoic acid methyl ester | 100 |
| 2 | (5Z,13E)-(8R,9S,11R,12R)-9,11-Dihydroxy-15,15-ethylenedioxy-16-phenoxy-17,18,19,20-tetranor-prostadienoic acid | 10 |
| 3 | (5Z,13E)-(8R,9S,11R,12R)-9,11-Dihydroxy-15,15-ethylenedioxy-16-phenoxy-17,18,19,20-tetranor-prostadienoic acid p-phenylphenacyl ester | 30 |
| 4 | (5Z,13E)-(8R,9S,11R,12R)-9,11-Dihydroxy-15,15-ethylenedioxy-17-phenyl-18,19,20-trinor-prostadienoic acid methyl ester | 30 |
| 5 | (5Z,13E)-(8R,9S,11R,12R)-9-Hydroxy-11-oxo-15,15-ethylenedioxy-16-phenoxy-17,18,19,20-tetranor-prostadienoic acid methyl ester | 10 |
| 6 | (5Z,13E)-(8R,9S,11R,12R)-9,11-Dihydroxy-15,15-ethylenedioxy-16-phenoxy-17,18,19,20-tetranor-prostadienoic acid butyl ester | 30 |
| 7 | (5Z,13E)-(8R,9S,11R,12R)-9,11-Dihydroxy-15,15-ethylenedioxy-17-phenyl-18,19,20-trinor-prostadienoic acid p-phenylphenacyl ester | 10 |
| 8 | (5Z,13E)-(8R,9S,11R,12R)-9,11-Dihydroxy-15,15-ethylenedioxy-15-(4-chlorophenyl)-16,17,18,19,20-pentanor-prostadienoic acid methyl ester | 10 |
| 9 | (5Z,13E)-(8R,9S,11R,12R)-9,11-Dihydroxy-15,15-ethylenedioxy-16-(4-fluorophenoxy)-17,18,19,20-tetranor-prostadienoic acid | 3 |
| 10 | (5Z,13E)-(8R,9S,11R,12R)-9,11-Dihydroxy-15,15-ethylenedioxy-15-(4-chlorophenyl)-16,17,18,19,20-pentanor-prostadienoic acid p-phenylphenacyl ester | 3 |
| 11 | (5Z,13E)-(8R,9S,11R,12R)-9,11-Dihydroxy-15,15-ethylenedioxy-16-(2-naphthyloxy)-17,18,19,20-tetranor-prostadienoic acid methyl ester | 3 |
| 12 | (5Z,13E)-(8R,9S,11R,12R)-9,11-Dihydroxy-15,15-ethylenedioxy-15-(4-chlorophenyl)-16,17,18,19,20-pentanor-prostadienoic acid (4-biphenylyl) ester | 3 |

As demonstrated by the table, the compounds of this invention, at doses one-third to one-hundredth the dose, are as effective in their abortive activity as 1 mg. of PG $F_{2\alpha}$ per animal.

The novel prostanoic acid derivatives, such as, for example (5Z,13E)-(8R,9S,11R,12R)-9,11-dihydroxy-15,15-ethylenedioxy-16-phenoxy-17,18,19,20-tetranor-prostadienoic acid methyl ester, are furthermore suitable for the synchronization of the sexual cycle in female mammals, such as cattle, monkeys, rabbits, pigs, sheep, etc. For practical application, the compounds of the present invention can be administered in dosages of 0.1 - 2 mg. per mammal, e.g., per head of cattle, for sexual cycle synchronization. Preferably, the active agent is given in liquid formulations, e.g., in oily solutions; if desired, solubilizers well-known to experts can also be added to these solutions. A mixture of benzyl benzoate/castor oil 1 : 3 is preferred.

The high dissociation of effectiveness of the compounds according to the present invention can be seen when testing is carried out on other smooth-muscular organs, such as, for example on the guinea pig ileum or in the isolated rabbit trachea, where a substantially lower stimulation can be observed than caused by the natural prostaglandins. The novel active agents of the PG E series show, on the isolated rabbit trachea in vitro, a bronchodilatatory effect and greatly inhibit the stomach acid secretion. Also, they act as a regulator in cardiac dysrhythmias. The novel compounds of the PG A and PG E series furthermore lower the blood pressure and have a diuretic effect.

The effective agents of this invention pertaining to the F series have a lesser bronchoconstrictive effect than natural prostaglandin $F_{2\alpha}$, which is of great advantage for their therapeutic use. For medical application, the active agents can be converted into a form suitable for inhalation, for oral or parenteral administration. For purposes of inhalation, aerosol or spray solutions are suitably prepared.

For oral administration, suitable are, for example, tablets, dragees, or capsules.

Sterile aqueous or oily solutions capable of being injected are utilized for parenteral application.

Thus, the present invention also relates to medicinal agents on the basis of compounds of general Formula I and customary auxiliary agents and vehicles.

The active agents of this invention are to serve, in conjunction with the adjuvants known and customary in galenic pharmacy, e.g., for the production of preparations to trigger abortion, for cycle control, or for the induction of labor. For this purpose, sterile aqueous solutions containing 0.01 - 10 μg./ml. of the active compound can be utilized as an intravenous infusion. For producing aqueous isotonic solutions, the acids and salts of general Formula I are especially suitable. In order to increase solubility, it is possible to add alcohols, such as ethanol and ethylene glycol.

The novel prostanoic acid derivatives exhibit a pharmacological spectrum of activity similar to that of the natural prostaglandins and are usable for similar purposes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the following examples are set forth in degrees Celsius.

EXAMPLE 1

(a)

(1S,5R,6R,7R)-6-[(E)-3,3-Ethylenedioxy-4-phenoxy-1-butenyl]-7-benzoyloxy-2-oxabicyclo[3,3,0]octan-3-one Formula III: A = trans-CH=CH; D = —$CH_2$—; E = —O—; $R_4$ = phenyl; Ac = benzoyl.

Two grams of (1S,5R,6R,7R)-6-[(E)-3-oxo-4-phenoxy-1-butenyl]-7-benzoyloxy-2;1 -oxabicyclo[3,3,0]octan-3-one (m.p. 134°; produced analogously to DOS 2,223,365), 5 ml. of ethylene glycol, and 30 mg. of p-toluenesulfonic acid were refluxed in 50 ml. of benzene for 6 hours with the use of a water trap. After cooling, the mixture was diluted with ether, shaken successively with sodium bicarbonate solution and water, dried with magnesium sulfate, and evaporated to dryness under vacuum. The oily residue was purified by column chromatography on silica gel. With ether/hexane (7 + 3), 1.8 g. of the title compound was eluted as a colorless oil.

IR (in $CHCl_3$): 1770, 1715, 1590, 1500, 970 $cm^{-1}$.

Analogously, the following ketals are produced from the corresponding unsaturated ketones:

(1S,5R,6R,7R)-6-[(E)-3,3-ethylenedioxy-3-(4-chlorophenyl)-1-propenyl]-7-benzoyloxy-2-oxabicyclo[3,3,0]-octan-3-one Formula III: A = trans-CH=CH; D-E-R$_4$ = 4-chlorophenyl; Ac = benzoyl. Melting point: 84.5°.

(The starting ketone, m.p. 128°-129°, was prepared analogously to DOS 2,322,142.)

(1S,5R,6R,7R)-6-[(E)-3,3-ethylenedioxy-1-decenyl]-7-benzoyloxy-2-oxabicyclo[3,3,0]octan-3-one.

Formula III: A = trans-CH=CH; D-E-R$_4$ = n-heptyl; Ac = benzoyl. Melting point: 92°.

(The starting ketone was produced analogously to DOS 2,150,361.)

(1S,5R,6R,7R)-6-[(E)-3,3-ethylenedioxy-4-propoxy-1-butenyl]-7-benzoyloxy-2-oxabicyclo[3,3,0]octan-3-one.

Formula III: A = trans-CH=CH; D = —CH$_2$—; E = —O—; R$_4$ = n-propyl; Ac = benzoyl. Colorless oil, IR: 1770, 1715, 1600, 1100, 970 cm$^{-1}$.

(The starting ketone, m.p. 74°, was prepared analogously to DOS 2,234,708.)

(1S,5R,6R,7R)-6-[(E)-3,3-ethylenedioxy-6-methoxy-1-hexenyl]-7-p-phenylbenzoyloxy-2-oxabicyclo[3,3,0]octan-3-one.

Formula III: A = trans-CH=CH; D = —CH$_2$—CH$_2$—CH$_2$—; E = —O—; R$_4$ = methyl; Ac = p-phenylbenzoyl. Melting point: 112°.

(The starting ketone, m.p. 79°, was produced analogously to DOS 2,327,813.)

(1S,5R,6R,7R)-6-[(E)-3,3-ethylenedioxy-5-phenyl-1-pentenyl]-7-benzoyloxy-2-oxabicyclo[3,3,0]octan-3-one.

Formula III: A = trans—CH=CH; D-E-R$_4$ = CH$_2$—CH$_2$—phenyl; Ac = benzoyl. Melting point: 135°.

(The starting ketone, m.p. 118°, was prepared analogously to DOS 2,234,709.)

(1S,5R,6R,7R)-6-[(E)-3,3-ethylenedioxy-4-(p-fluorophenoxy)-1-butenyl]-7-benzoyloxy-2-oxabicyclo[3,3,0]octan-3-one.

Formula III: A = trans-CH=CH; D = —CH$_2$—; E = —O—; R$_4$ = p-fluorophenyl; Ac = benzoyl. Colorless oil, IR: 1770, 1715, 1600, 1500, 975 cm$^{-1}$.

(The starting ketone, m.p. 123°, was prepared analogously to DOS 2,223,365.)

(1S,5R,6R,7R)-6-[(E)-3,3-ethylenedioxy-4-(p-chlorophenoxy)-1-butenyl]-7-benzoyloxy-2-oxabicyclo[3,3,0]octan-3-one.

Formula III: A = trans-CH=CH; D = —CH$_2$—; E = —O—; R = p-chlorophenyl; Ac = benzoyl. Melting point: 75°.

(The starting ketone, m.p. 130°, was prepared analogously to DOS 2,223,365.)

(1S,5R,6R,7R)-6-[(E)-3,3-ethylenedioxy-4-(2-naphthoyloxy)-1-butenyl]-7-benzoyloxy-2-oxabicyclo[3,3,0]octan-3-one.

Formula III: A = trans-CH=CH; D = —CH$_2$—; E = —O—; R$_4$ = 2-naphthyl; Ac = benzoyl. Melting point: 108°.

(The starting ketone, m.p. 126°, was produced in analogy to DOS 2,223,365.)

(1S,5R,6R,7R)-6-[(E)-3,3-ethylenedioxy-3-(1,3-dioxa-2-indanyl)-1-propenyl]-7-benzoyloxy-2-oxabicyclo[3,3,0]octan-3-one.

Formula III: A = trans-CH=CH;

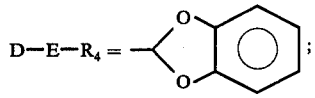

Ac = benzoyl. Melting point: 113.5°.

(The starting ketone, m.p. 119°, was produced as disclosed in DOS 2,365,101.)

(1S,5R,6R,7R)-6-[(E)-3,3-ethylenedioxy-3-(4-biphenylyl)-1-propenyl]-7-p-phenylbenzoyloxy-2-oxabicyclo[3,3,0]octan-3-one.

Formula III: A = trans-CH=CH;

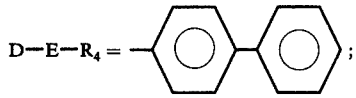

Ac = p-phenylbenzoyl. Melting point: 153°.

(The starting ketone, m.p. 215°, was produced analogously to DOS 2,322,142.)

(b)
(2RS,3aR,4R,5R,6aS)-4-[(E)-3,3-Ethylenedioxy-4-phenoxy-1-butenyl]-2,5-dihydroxyperhydrocyclopenta[b]furan Formula IV: A = trans—CH=CH; D = —CH$_2$—; E = —O—; R$_4$ = phenyl.

14 ml. of a 20% solution of diisobutylaluminum hydride in toluene was dropped at −60° under argon to a solution of 1.5 g. of (1S,5R,6R,7R)-6-[(E)-3,3-ethylenedioxy-4-phenoxy-1-butenyl]-7-benzoyloxy-2-oxabicyclo[3,3,0]octan-3-one (Example 1[a]) in 90 ml. of absolute toluene. After 30 minutes, the reaction was terminated by adding 4 ml. of isopropanol dropwise, and the mixture was then stirred for 30 minutes at 0° while adding 100 ml. of brine. Subsequently, the mixture was extracted with ethyl acetate, shaken with brine, dried with magnesium sulfate, and evaporated under vacuum. By filtration of the residue with ether over 30 g. of silica gel, 1.02 g. of the title compound was obtained as a colorless oil.

IR: 3600, 1500, 970 cm$^{-1}$.

Analogously, the following lactols are obtained from the corresponding lactones (prepared according to Example 1[a]):

(2RS,3aR,4R,5R,6aS)-4-[(E)-3,3-ethylenedioxy-3-(4-chlorophenyl)-1-propenyl]-2,5-dihydroxyperhydrocyclopenta[b]furan. Formula IV: A = trans—CH=CH; D-E-R$_4$ = 4-chlorophenyl. Colorless oil; IR: 3600,1600,1490,975 cm$^{-1}$.

(2RS,3aR,4R,5R,6aS)-4-[(E)-3,3-ethylenedioxy-1-decenyl]-2,5-dihydroxyperhydrocyclopenta[b]furan. Formula IV: A = trans—CH=CH; D-E-R$_4$ = n-heptyl. Colorless oil; IR: 3600,970 cm$^{-1}$.

(2RS,3aR,4R,5R,6aS)-4-[(E)-3,3-ethylenedioxy-4-n-propoxy-1-butenyl]-2,5-dihydroxyperhydrocyclopenta[b]furan.

Formula IV: A = trans-CH=CH; D = —CH$_2$—; E = —O—; R$_4$ = n-propyl. Colorless oil; IR: 3600,1105,978 cm$^{-1}$.

(2RS,3aR,4R,5R,6aS)-4-[(E)-3,3-ethylenedioxy-6-methoxy-1-hexenyl]-2,5-dihydroxyperhydrocyclopenta[b]furan.

Formula IV: A = trans-CH=CH; D CH₂—CH₂—CH₂; E = —O—; R₄ = methyl. Colorless oil; IR: 3600,1100,970 cm⁻¹.

(2RS,3aR,4R,5R,6aS)-4-[(E)-3,3-ethylenedioxy-5-phenyl-1-pentenyl]-2,5-dihydroxyperhydrocyclopenta[b]furan.

Formula IV: A = trans—CH=CH; D-E-R₄ = CH₂-CH₂-phenyl. Colorless oil; IR: 3600,1600,970 cm⁻¹.

(2RS,3aR,4R,5R,6aS)-4-[(E)-3,3-ethylenedioxy-4-(p-fluorophenoxy)-1-butenyl]-2,5-dihydroxyperhydrocyclopenta[b]furan. Formula IV: A = trans—CH=CH; D = —CH₂—; E = —O—; R₄ = p-fluorophenyl. Colorless oil; IR: 3600,1500,970 cm⁻¹.

(2RS,3aR,4R,5R,6aS)-4-[(E)-3,3-ethylenedioxy-4-(p-chlorophenoxy)-1-butenyl]-2,5-dihydroxyperhydrocyclopenta[b]furan. Formula IV: A = trans—CH=CH; D = —CH₂—; E = —O—; R₄ = p-chlorophenyl. Colorless oil; IR: 3600,1500,970 cm⁻¹.

(2RS,3aR,4R,5R,6aS)-4-[(E)-3,3-ethylenedioxy-4-(2-naphthyloxy)-1-butenyl]-2,5-dihydroxyperhydrocyclopenta[b]furan. Formula IV: A = trans—CH=CH; D = —CH₂—; E = —O—; R₄ = 2-naphthyl. Colorless oil; IR: 3600,1630,1600,975 cm⁻¹.

(2RS,3aR,4R,5R,6aS)-4-[(E)-3,3-ethylenedioxy-3-(1,3-dioxa-2-indanyl)-1-propenyl]-2,5-dihydroxyperhydrocyclopenta[b]furan. Formula IV: A = trans—CH=CH;

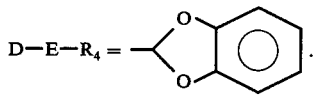

Colorless oil; IR: 3600,1495,970 cm⁻¹.

(2RS,3aR,4R,5R,6aS)-4-[(E)-3,3-ethylenedioxy-3-(4-biphenylyl)-1-propenyl]-2,5-dihydroxyperhydrocyclopenta[b]furan. Formula IV: A = trans—CH=CH;

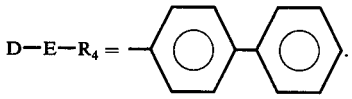

Colorless oil; IR: 3600,1595,1490,970,840 cm⁻¹.

(c)
(5Z,13E)-(8R,9S,11R,12R)-9,11-Dihydroxy-15,15-ethylenedioxy-16-phenoxy-17,18,19,20-tetranor-prostadienoic Acid Formula Ia: A = trans—CH=CH; R₁ = H; D = CH₂; E = —O—; R₄ = phenyl.

At 15°, 82 ml. of a solution of methanesulfinylmethylsodium in absolute dimethyl sulfoxide (prepared from 4.08 g. of 50% sodium hydride suspension in mineral oil in 82 ml. of dimethyl sulfoxide and heating to 70° for one hour) was added dropwise to a solution of 21 g. of 4-carboxybutyltriphenylphosphonium bromide in 80 ml. of absolute dimethyl sulfoxide. The mixture was agitated for 30 minutes at room temperature. The red ylene solution was dropped at 15° to a solution of 3.03 g. of (2RS,3aR,4R,5R,6aS)-4-[(E)-3,3-ethylenedioxy-4-phenoxy-1-butenyl]-2,5-dihydroxyperhydrocyclopenta[b]furan (prepared according to Example 1[b]) in 40 ml. of absolute dimethyl sulfoxide and stirred for 2 hours at 50°. After removing the solvent by evaporation under vacuum (0.01 torr [mm. Hg]), the residue was dissolved in 100 ml. of water, extracted three times with respectively 80 ml. of ether, and the ether extract was discarded. The aqueous phase was adjusted to pH 4–5 with 10% citric acid solution and extracted four times with a mixture of ether/hexane (2 + 1). The organic phase was shaken with brine, dried with magnesium sulfate, and evaporated under vacuum. After chromatography of the residue on silica gel (chloroform/isopropanol = 5 + 1), 2.25 g. of the title compound was obtained as a colorless oil. IR: 3600–3400,1720,1600,1490,970 cm⁻¹.

Analogously, the following prostadienoic acids are obtained from the corresponding lactols (produced according to Example 1[b]):

(5Z,13E)-(8R,9S,11R,12R)-9,11-dihydroxy-15,15-ethylenedioxy-15-(4-chlorophenyl)-16,17,18,19,20-pentanor-prostadienoic acid Formula Ia: A = trans—CH=CH; R₁ = H; D—E—R₄ = 4-chlorophenyl. Colorless oil; IR: 3600–3400,1720,1600,1490,970 cm⁻¹.

(5Z,13E)-(8R,9S,11R,12R)-9,11dihydroxy-15,15-ethylenedioxy-20-ethyl-prostadienoic acid. Formula Ia: A = trans—CH=CH; R₁ = H; D—E—R₄ = n-heptyl. Melting point: 94°; IR: 3600–3400,1720,970 cm⁻¹.

(5Z,13E)-(8R,9S,11R,12R)-9,11-dihydroxy-15,15-ethylenedioxy-16-n-propoxy-17,18,19,20-tetranor-prostadienoic acid. Formula Ia: A = trans—CH=CH; R₁ H; D = —CH₂—; E = —O—; R₄ = n-propyl. Colorless oil; IR: 3600–3400,1720,1100,978 cm⁻¹.

(5Z,13E)-(8R,9S,11R,12R)-9,11-dihydroxy-15,15-ethylenedioxy-19-oxa-prostadienoic acid. Formula Ia: A = trans—CH=CH; R₁ = H; D = —CH₂—CH₂—CH₂—; E= —O—; R₄= methyl. Colorless oil; IR: 3600–3400,1718,1600,970 cm⁻¹.

(5Z,13E)-(8R,9S,11R,12R)-9,11-dihydroxy-15,15-ethylenedioxy-16-(4-fluorophenoxy)-17,18,19,20-tetranor-prostadienoic acid. Formula Ia: A = trans—CH=CH; R₁ = H; D = —CH₂—; E = —O—; R₄ = p-fluorophenyl. Colorless oil; IR: 3600–3300,1720,1500,970 cm⁻¹.

(5Z,13E)-(8R,9S,11R,12R)-9,11-dihydroxy-15,15-ethylenedioxy-16-(4-chlorophenoxy)-17,18,19,20-tetranor-prostadienoic acid. Formula Ia: A = trans—CH=CH; R₁ = H; D = —CH₂—; E = —O—; R₄ = p-chlorophenyl. Colorless oil; IR: 3600–3400,1720,1500,970 cm⁻¹.

(5Z,13E)-(8R,9S,11R,12R)-9,11-dihydroxy-15,15-ethylenedioxy-16-(2-naphthyloxy)-17,18,19,20-tetranor-prostadienoic acid. Formula Ia: A = trans—CH=CH; R₁ = H; D = —CH₂—; E = —O—; R₄ = 2-naphthyl. Colorless oil; IR: 3600–3400,1720,1630,1600,978 cm⁻¹.

(5Z,13E)-(8R,9S,11R,12R)-9,11-dihydroxy-15,15-ethylenedioxy-15-(1,3-dioxa-2-indanyl)-16,17,18,19,20-pentanor-prostadienoic acid. Formula Ia: A = trans—CH=CH; R₁ = H;

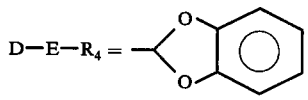

Colorless oil; IR: 3600–3400,1725,1495,970 cm⁻¹.

(5Z,13E)-(8R,9S,11R,12R)-9,11-dihydroxy-15,15-ethylenedioxy-15-(4-biphenylyl)-16,17,18,19,20-pentanor-prostadienoic acid. Formula Ia: A = trans—CH=CH; R₁ = H;

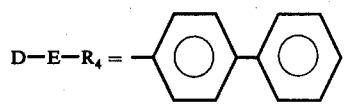

Colorless oil; IR: 3600–3400,1720,1600,1485,970,845 cm$^{-1}$.

EXAMPLE 2

(a)

(1S,5R,6R,7R)-6-(3,3-Ethylenedioxy-4-phenoxy-1-butyl)-7-benzoyloxy-2-oxabicyclo[3,3,0]octan-3-one Formula III: A = —CH$_2$—CH$_2$—; D = —CH$_2$—; E = —O—; R$_4$ = phenyl; Ac = benzoyl.

Three grams of (1S,5R,6R,7R)-6-(3-Oxo-4-phenoxy-1-butyl)-7-benzoyloxy-2-oxabicyclo[3,3,0]octan-3-one (produced analogously to DOS 2,223,365), 7.5 ml. of ethylene glycol, and 45 mg. of toluenesulfonic acid were refluxed in 75 ml. of benzene for 4 hours with the use of a water trap. After cooling, the mixture was introduced into sodium bicarbonate solution, extracted with ether, dried over magnesium sulfate, and evaporated to dryness under vacuum. The oily residue was filtered over 30 g. of silica gel with ether/hexane (7 + 3). Yield: 2.73 g. of the title compound as a colorless oil. IR: 1770,1715,1590,1500 cm$^{-1}$.

Analogously, the following ketals are produced from the corresponding saturated ketones:

(1S,5R,6R,7R)-6-[3,3-ethylenedioxy-3-(4-chlorophenyl)-1-propyl]-7-benzoyloxy-2-oxabicyclo[3,3,0]octan-3-one. Formula III: A = —CH$_2$—CH$_2$—; D-E-R$_4$ = 4-chlorophenyl; Ac = benzoyl. Colorless oil; IR: 1770,1715,1600,1490 cm$^{-1}$.

(The starting ketone was prepared analogously to DOS 2,322,142.)

(1S,5R,6R,7R)-6-(3,3-ethylenedioxy-5-phenyl-1-pentyl)-7-benzoyloxy-2-oxabicyclo[3,3,0]octan-3-one. Formula III: A = —CH$_2$—CH$_2$—; D-E-R$_4$ = CH$_2$—CH$_2$-phenyl; Ac = benzoyl. Colorless oil; IR: 1770,1715,1600 cm$^{-1}$.

(The starting ketone was prepared in analogy to DOS 2,234,709.)

(1S,5R,6R,7R)-6-[3,3-ethylenedioxy-4-(p-fluorophenoxy)-1-butyl]-7-benzoyloxy-2-oxabicyclo[3,3,0]octan-3-one. Formula III: A = —CH$_2$—CH$_2$—; D = —CH$_2$—; E = —O—; R$_4$ = p-fluorophenyl; Ac = benzoyl. Colorless oil; IR: 1770,1715,1500 cm$^{-1}$.

(The starting ketone was produced analogously to DOS 2,223,365.)

(1S,5R,6R,7R)-6-[3,3,-ethylenedioxy-4-(p-chlorophenoxy)-1-butyl]-7-benzoyloxy-2-oxabicyclo[3,3,0]octan-3-one. Formula III: A = —CH$_2$—CH$_2$—; D = —CH$_2$—; E = —O—; R$_4$ = p-chlorophenyl; Ac = benzoyl. Colorless oil; IR: 1770,1715,1498 cm$^{-1}$.

(The starting ketone was prepared analogously to DOS 2,223,365.)

(1S,5R,6R,7R)-6-[3,3-ethylenedioxy-4-(2-naphthyloxy)-1-butyl]-7-benzoyloxy-2-oxabicyclo[3,3,0]octan-3-one. Formula III: A = —CH$_2$—CH$_2$—; D = —CH$_2$—; E = —O—; R$_4$ = 2-naphthyl; Ac = benzoyl. Colorless oil; IR: 1765,1715,1630,1600 cm$^{-1}$.

(The starting ketone was prepared analogously to DOS 2,223,365.)

(b)

(2RS,3aR,4R,5R,6aS)-4-(3,3-Ethylenedioxy-4-phenoxy-1-butyl)-2,5-dihydroxyperhydrocyclopenta[b]furan Formula IV: A = —CH$_2$—CH$_2$—; D = —CH$_2$—; E = —O—; R$_4$ = phenyl.

At −60° under argon, 16 ml. of a 20% solution of diisobutylaluminum hydride in toluene was added dropwise to a solution of 1.65 g. of (1S,5R,6R,7R)-6-(3,3-ethylenedioxy-4-phenoxy-1-butyl)-7-benzoyloxy-2-oxabicyclo[3,3,0]octan-3-one (produced in accordance with Example 2[a]) in 100 ml. of absolute toluene; the mixture was stirred for 30 minutes. By the dropwise addition of 5 ml. of isopropanol, the reaction was terminated, and the mixture was stirred for 30 minutes at 0° while adding 100 ml. of brine. Then, the mixture was extracted with ethyl acetate, shaken with brine, dried with magnesium sulfate, and evaporated under vacuum. Filtration of the residue with ether over 35 g. of silica gel yielded 1.1 g. of the title compound as a colorless oil. IR: 3600,1500 cm$^{-1}$.

In an analogous manner, the following lactols are produced from the corresponding lactones (prepared according to Example 2[a]):

(2RS,3aR,4R,5R,6aS)-4-[3,3-ethylenedioxy-3-(4-chlorophenyl)-1-propyl]-2,5-dihydroxyperhydrocyclopenta[b]furan. Formula IV: A = —CH$_2$—CH$_2$—; D-E-R$_4$ = 4-chlorophenyl. Colorless oil; IR: 3600,1600,1490 cm$^{-1}$. (2RS,3aR,4R,5R,6aS)-4-(3,3-ethylenedioxy-5-phenyl-1-pentyl)-2,5-dihydroxyperhydrocyclopenta[b]furan. Formula IV: A = —CH$_2$—CH$_2$—; D-E-R$_4$ = CH$_2$—CH$_2$-phenyl. Colorless oil; IR: 3600,1600 cm$^{-1}$.

(2RS,3aR,4R,5R,6aS)-4-[3,3-ethylenedioxy-4-(p-fluorophenoxy)-1-butyl]-2,5-dihydroxyperhydrocyclopenta[b]furan. Formula IV: A = —CH$_2$—CH$_2$—; D = —CH$_2$—; E = —O—; R$_4$ = p-fluorophenyl. Colorless oil; IR: 3600,1500 cm$^{-1}$.

(2RS,3aR,4R,5R,6aS)-4-[3,3-ethylenedioxy-4-(p-chlorophenoxy)-1-butyl]-2,5-dihydroxyperhydrocyclopenta[b]furan. Formula IV: A = —CH$_2$—CH$_2$—; D = —CH$_2$—; E = —O—; R$_4$ = p-chlorophenyl. Colorless oil; IR: 3600,1500 cm$^{-1}$.

(2RS,3aR,4R,5R,6aS)-4-[3,3-ethylenedioxy-4-(2-naphthyloxy)-1-butyl]-2,5-dihydroxyperhydrocyclopenta[b]furan. Formula IV: A = —CH$_2$—CH$_2$—; D = —CH$_2$—; E = —O—; R$_4$ = 2-naphthyl. Colorless oil; IR: 3600,1630,1600 cm$^{-1}$.

(c)

(5Z)-(8R,9S,11R,12R)-9,11-Dihydroxy-15,15-ethylenedioxy-16-phenoxy-17,18,19,20-tetranor-prostenoic Acid Formula Ia: A = —CH$_2$—CH$_2$—; R$_1$ = H; D = —CH$_2$—; E = —O—; R$_4$ = phenyl.

At 15°, 55 ml. of a solution of methanesulfinylmethylsodium in absolute dimethyl sulfoxide (produced by stirring 2.74 g. of 50% sodium hydride suspension [in mineral oil] for 1 hour at 70° in 55 ml. of absolute dimethyl sulfoxide) was added dropwise to a solution of 14 g. of 4-carboxybutyltriphenylphosphonium bromide in 60 ml. of absolute dimethyl sulfoxide; the mixture was agitated for 20 minutes at room temperature. The red ylene solution was dropped at 15° to a solution of 2 g. of (2RS,3aR,4R,5R,6aS)-4-(3,3-ethylenedioxy-4-phenoxy-1-butyl)-2,5-dihydroxyperhydrocyclopenta[b]furan (prepared according to Example 2[b]) in 30 ml. of absolute dimethyl sulfoxide, and the mixture was stirred for 2 hours at 50°. After the solvent had been evaporated under vacuum (about 0.01 torr), the residue was dissolved in 70 ml. of water, extracted three times with ether, and the ether extract was discarded. The aqueous phase was adjusted to pH 4–5 with 10% citric acid and extracted four times with ether/hexane mixture (2 + 1). The organic phase was shaken with brine and evaporated under vacuum. After chromatographing the residue on silica gel with methylene chloride/isopropanol (5 + 1), 1.49 g. of the title compound was obtained as an oil having a slightly yellow color. IR: 3600–3400,1720,1600,1490 cm$^{-1}$.

Analogously, the following prostenoic acids are obtained from the corresponding lactols (prepared according to Example 2[b]):

(5Z)-(8R,9S,11R,12R)-9,11-dihydroxy-15,15-ethylenedioxy-15-(4-chlorophenyl)-16,17,18,19,20-pentanor-prostenoic acid. Formula Ia: A = —CH$_2$—CH$_2$—; R$_1$ = H; D-E-R$_4$ = 4-chlorophenyl. Colorless oil; IR: 3600–3400,1718,1600,1495 cm$^{-1}$.

(5Z)-(8R,9S,11R,12R)-9,11-dihydroxy-15,15-ethylenedioxy-17-phenyl-18,19,20-trinor-prostenoic acid. Formula Ia: A = —CH$_2$—CH$_2$—; R$_1$ = H; D-E-R$_4$ = —CH$_2$—CH$_2$-phenyl. Colorless oil; IR: 3600–3400,1716,1600 cm$^{-1}$.

(5Z)-(8R,9S,11R,12R)-9,11-dihydroxy-15,15-ethylenedioxy-16-(4-fluorophenoxy)-17,18,19,20-tetranor-prostenoic acid. Formula Ia: A = —CH$_2$—CH$_2$—; D = —CH$_2$—; E = —O—; R$_4$ = 4-fluorophenyl. Yellowish oil; IR: 3600–3300,1720,1500 cm$^{-1}$.

(5Z)-(8R,9S,11R,12R)-9,11-dihydroxy-15,15-ethylenedioxy-16-(4-chlorophenoxy)-17,18,19,20-tetranor-prostenoic acid. Formula Ia: A = —CH$_2$—CH$_2$—; R$_1$ = H; D = —CH$_2$—; E = —O—; R$_4$ = 4-chlorophenyl. Colorless oil; IR: 3600–3400,1720,1500 cm$^{-1}$.

(5Z)-(8R,9S,11R,12R)-9,11-dihydroxy-15,15-ethylenedioxy-16-(2-naphthyloxy)-17,18,19,20-tetranor-prostenoic acid. Formula Ia: A = —CH$_2$—CH$_2$—; R$_1$ = H; D = —CH$_2$—; E = —O—; R$_4$ = 2-naphthyl. Colorless, viscous matter; IR: 3600–3400,1718,1630,1600 cm$^{-1}$.

EXAMPLE 3

(5Z,13E)-(8R,11R,12R)-11-Hydroxy-9-oxo-15,15-ethylenedioxy-16-phenoxy-17,18,19,20-tetranor-prostadienoic Acid Formula I: R$_1$ = H; R$_2$ and R$_3$ = O; R$_4$ = phenyl; A = trans—CH=CH; B = cis—CH=CH; D = —CH$_2$—; E = —O—;

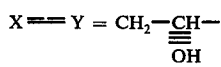

Under a hydrogen atmosphere, 1.60 g. of platinum dioxide was shaken in 30 ml. of ethyl acetate for 1.5 hours. After the hydrogen was displaced by nitrogen, the mixture was shaken for 3 hours under an oxygen atmosphere, then combined with a solution of 206 mg. of (5Z,13E)-(8R,9S,11R,12R)-9,11-dihydroxy-15,15-ethylenedioxy-16-phenoxy-17,18,19,20-tetranorprostadienoic acid in 3 ml. of ethyl acetate. The mixture was agitated for 48 hours at room temperature under an oxygen atmosphere, then filtered and evaporated under vacuum. After chromatography on 25 g. of silica gel (ether/dioxane = 8 + 2), 105 mg. of the title compound was obtained as a colorless oil; IR: 3600–3300,1740,1710,1600,1498,975 cm$^{-1}$.

Analogously, the following PG'E$_2$ derivatives are produced from the corresponding PG'F$_{2\alpha}$ derivatives (prepared according to Examples 1 and 2):

(5Z,13E)-(8R,11R,12R)-11-hydroxy-9-oxo-15,15-ethylenedioxy-15-(4-chlorophenyl)-16,17,18,19,20-pentanor-prostadienoic acid. Formula I: R$_1$ = H; R$_2$ and R$_3$ = O; D-E-R$_4$ = 4-chlorophenyl; A = trans-CH=CH; B = cis—CH=CH;

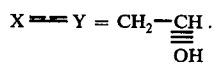

Slightly yellow-colored oil; IR: 3600–3300,1740,1715,1600,1485,970 cm$^{-1}$.

(5Z,13E)-(8R,11R,12R)-11-hydroxy-9-oxo-15,15-ethylenedioxy-20-ethyl-prostadienoic acid. Formula I: R$_1$ = H; R$_2$ and R$_3$ = O; D-E-R$_4$ = n-heptyl; A = trans—CH=CH; B = cis—CH=CH;

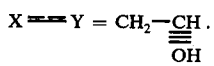

Colorless oil; IR: 3600–3300,1740,1710,978 cm$^{-1}$.

(5Z,13E)-(8R,11R,12R)-11-hydroxy-9-oxo-15,15-ethylenedioxy-16-n-propoxy-17,18,19,20-tetranor-prostadienoic acid. Formula I: R$_1$ = H; R$_2$ and R$_3$ = O; D = —CH$_2$—; E = —O—; R$_4$ = n-propyl; A = trans—CH=CH; B = cis—CH=CH;

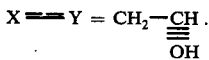

Colorless oil; IR: 3600–3300,1740,1715,1100,975 cm$^{-1}$.

(5Z,13E)-8R,11R,12R)-11-hydroxy-9-oxo-9-oxo-15,15-ethylenedioxy-19-oxa-prostadienoic acid. Formula I: R$_1$ = H; R$_2$ and R$_3$ = O; D = —CH$_2$—CH$_2$—CH$_2$—; E = —O—; R$_4$ = methyl; A = trans—CH=CH; B = cis—CH=CH;

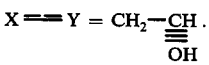

Colorless oil; IR: 3600–3400,1740,1715,1100,973 cm$^{-1}$.

(5Z,13E)-(8R,11R,12R)-11-hydroxy-9-oxo-15,15-ethylenedioxy-17-phenyl-18,19,20-trinor-prostadienoic acid. Formula I: R$_1$ = H; R$_2$ and R$_3$ = O; D-E-R$_4$ = —CH$_2$—CH$_2$-phenyl; A = trans—CH=CH; B = cis—CH=CH;

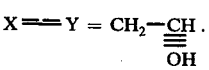

Colorless oil; IR: 3600–3400,1740,1715,1600,975 cm$^{-1}$.

(5Z,13E)-(8R,11R,12R)-11-hydroxy-9-oxo-15,15-ethylenedioxy-16-(4-fluorophenoxy)-17,18,19,20-tetranor-prostadienoic acid. Formula I: R$_1$ = H; R$_2$ and R$_3$ = O; R$_4$ = 4-fluorophenyl; A = trans—CH=CH; B = cis—CH=CH; D = —CH$_2$—; E = —O—;

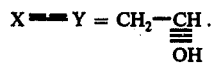

Colorless oil; IR: 3600–3400,1735,1710,1500,970 cm$^{-1}$.

(5Z,13E)-(8R,11R,12R)-11-hydroxy-9-oxo-15,15-ethylenedioxy-16-(4-chlorophenoxy)-17,18,19,20-tetranor-prostadienoic acid. Formula I: $R_1$ = H; $R_2$ and $R_3$ = O; $R_4$ = 4-chlorophenyl; A = trans—CH=CH; B = cis—CH=CH; D = —CH$_2$—; E — O—;

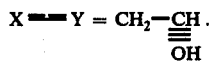

Colorless oil; IR: 3600–3300,1740,1710,1500,970 cm$^{-1}$.

(5Z,13E)-(8R,11R,12R)-11-hydroxy-9-oxo-15,15-ethylenedioxy-16-(2-naphthyloxy)-17,18,19,20,-tetranor-prostadienoic acid. Formula I: $R_1$ = H; $R_2$ and $R_3$ = O; $R_4$ = 2-naphthyl; A = trans—CH=CH; B = cis—CH=CH; D = —CH$_2$—; E = —O—;

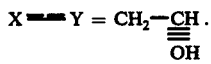

Colorless oil; IR: 3600–3400,1740,1710,1630,1600,978 cm$^{-1}$.

(5Z,13E)-(8R,11R,12R)-11-hydroxy-9-oxo-15,15-ethylenedioxy-15-(1,3-dioxa-2-indanyl)-16,17,18,19,20-pentanor-prostadienoic acid. Formula I: $R_1$ = H; $R_2$ and $R_3$ = O;

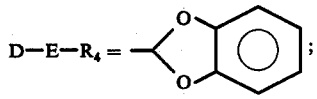

A = trans—CH=CH; B = cis—CH=CH;

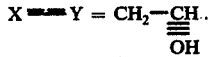

Slightly yellow-colored oil; IR: 3600–3400,1740,1715,1495,975 cm$^{-1}$.

(5Z,13E)-(8R,11R,12R)-11-hydroxy-9-oxo-15,15-ethylenedioxy-15-(4-biphenylyl)-16,17,18,19,20-pentanor-prostadienoic acid, Formula I: $R_1$ = H; $R_2$ and $R_3$ = O;

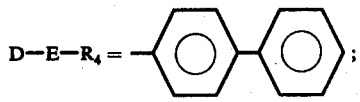

A = trans-CH=CH; B = cis-CH=CH;

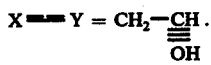

Colorless oil; IR: 3600–3400, 1740, 1710, 1600, 1485, 970, 845 cm$^{-1}$.

(5Z)-(8R,11R,12R)-11-hydroxy-9-oxo-15,15-ethylenedioxy-16-phenoxy-17,18,19,20-tetranor-prostenoic acid, Formula I: $R_1$ = H; $R_2$ and $R_3$ = O; $R_4$ = phenyl; A = —CH$_2$—CH$_2$—; B = cis-CH=CH; D = —CH$_2$—; E = —O—;

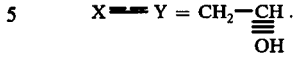

Colorless oil; IR: 3600–3400, 1735, 1715, 1600, 1490 cm$^{-1}$.

(5Z)-(8R,11R,12R)-11-hydroxy-9-oxo-15,15-ethylenedioxy-15-(4-chlorophenyl)-16,17,18,19,20-pentanor-prostenoic acid, Formula I: $R_1$ = H; $R_2$ and $R_3$ = O; D-E-$R_4$ = 4-chlorophenyl; A = —CH$_2$—CH$_2$—; B = cis-CH=CH;

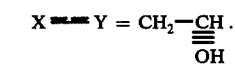

Slightly yellow-colored oil; IR: 3600–3400, 1740, 1715, 1600, 1495 cm$^{-1}$.

(5Z)-(8R,11R,12R)-11-hydroxy-9-oxo-15,15-ethylenedioxy-17-phenyl-18,19,20-trinor-prostenoic acid, Formula I: $R_1$ = H; $R_2$ and $R_3$ = 0; D-E-$R_4$ = CH$_2$-CH$_2$-phenyl; A = —CH$_2$—CH$_2$—; B = cis-CH=CH;

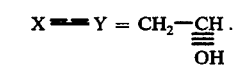

Colorless oil; IR: 3600–3400, 1735, 1710, 1600 cm$^{-1}$.

(5Z)-(8R,11R,12R)-11-hydroxy-9-oxo-15,15-ethylenedioxy-16-(4-fluorophenoxy)-17,18,19,20-tetranor-prostenoic acid, Formula I: $R_1$ = H; $R_2$ and $R_3$ = O; $R_4$ = 4-fluorophenyl; A = —CH$_2$—CH$_2$—; B = cis-CH=CH; D = —CH$_2$—; E = —O—;

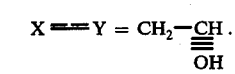

Colorless oil; IR: 3600–3400, 1735, 1710, 1500 cm$^{-1}$.

(5Z)-(8R,11R,12R)-11-hydroxy-9-oxo-15,15-ethylenedioxy-16-(4-chlorophenoxy)-17,18,19,20-tetranor-prostenoic acid, Formula I: $R_1$ = H; $R_2$ and $R_3$ = O; $R_4$ = 4-chlorophenyl; A = —CH$_2$—CH$_2$—; B = cis-CH=CH; D = —CH$_2$—; E = —O—;

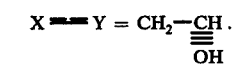

Colorless oil; IR: 3600–3400, 1735, 1712, 1500 cm$^{-1}$.

(5Z)-(8R,11R,12R)-11-hydroxy-9-oxo-15,15-ethylenedioxy-16-(2-naphthyloxy)-17,18,19,20-tetranor-prostenoic acid, Formula I: $R_1$ = H; $R_2$ and $R_3$ = O; $R_4$ = 2-naphthyl; A = —CH$_2$—CH$_2$—; B = cis-CH=CH; D = —CH$_2$—; E = —O—;

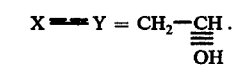

Yellowish oil; IR: 3600–3300, 1740, 1714, 1630, 1600 cm$^{-1}$.

EXAMPLE 4

(5Z,13E)-(8R,9S,12R)-9-Hydroxy-11-oxo-15,15-ethylenedioxy-16-phenoxy-17,18,19,20-tetranor-prostadienoic Acid Formula I: $R_1 = R_3 = H$; $R_2 = OH$; $R_4 = $ phenyl; A = trans-CH=CH; B = cis-CH=CH; D = —CH$_2$—; E = —O—;

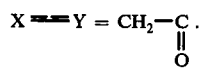

$$X = Y = CH_2 - \underset{\underset{O}{\|}}{C}.$$

At −20°, 0.23 ml. of Jones reagent (J. Chem. Soc. 1953, 2555) was added to a solution of 346 mg. of (5Z,13E)-(8R,9S,11R,12R)-9,11-dihydroxy-15,15-ethylenedioxy-16-phenoxy-17,18,19,20-tetranor-prostadienoic acid in 10 ml. of acetone. The mixture was stirred for 30 minutes at −20°, then diluted with ether, shaken several times with brine, dried over magnesium sulfate, and evaporated under vacuum. The residue was purified by preparative layer chromatography on silica gel plates (eluent: ether/dioxane 9 + 1), thus obtaining 160 mg. of the title compound as a viscous, colorless oil. IR: 3600–3400, 1740, 1710, 1600, 1495, 970 cm$^{-1}$.

Analogously, the following PG D$_2$ derivatives are produced from the corresponding PG'F$_{2\alpha}$ derivatives (prepared according to Examples 1 and 2):

(5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z, 13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid and (5A)-(8R,9S,12R)-9-hydroxy-11-oxo-15,15-ethylenedioxy-16-(2-naphthyloxy)-17,18,19,20-tetranor-prostenoic acid.

EXAMPLE 5

(a)

(1S,5R,6R,7R)-6-[(E)-3,3-Ethylenedioxy-4-(2-naphthyloxy)-1-butenyl]-7-hydroxy-2-oxabicyclo[3,3,0]octan-3-one Formula VI: D = —CH$_2$—; E = —O—; $R_4$ = 2-naphthyl A mixture of 500 mg. of (1S,5R,6R,7R)-6-[(E)-3,3-ethylenedioxy-4-(2-naphthyloxy)-1-butenyl]-7-benzoyloxy-2-oxabicyclo[3,3,0]octan-3-one (prepared according to Example 1[a]), 138 mg. of anhydrous potassium carbonate, and 20 ml. of methanol was stirred for 2 hours at room temperature under an argon atmosphere. The mixture was then diluted with 20 ml. of 0.1N hydrochloric acid, agitated for 10 minutes, diluted with brine, and extracted with methylene chloride. The organic phase was washed with brine, dried over magnesium sulfate, and evaporated under vacuum. The residue was recrystallized from diisopropyl ether/methylene chloride, thus obtaining 290 mg. of the title compound as colorless crystals, m.p. 159°. IR: 3600, 1770, 1630, 1600, 1510, 977 cm$^{-1}$.

Analogously, the following alcohols are produced from the corresponding benzoates:

(1S,5R,6R,7R)-6-[(E)-3,3-ethylenedioxy-4-phenoxy-1-butenyl]-7-hydroxy-2-oxabicyclo[3,3,0]octan-3-one, IR: 3600, 1770, 1590, 1500, 975 cm$^{-1}$.

(1S,5R,6R,7R)-6-[(E)-3,3-ethylenedioxy-4-(4-fluorophenoxy)-1-butenyl]-7-hydroxy-2-oxabicyclo[3,3,0]octan-3-one, IR: 3600, 1770, 1595, 1500, 975 cm$^{-1}$.

(1S,5R,6R,7R)-6-[(E)-3,3-ethylenedioxy-4-(4-chlorophenoxy)-1-butenyl]-7-hydroxy-2-oxabicyclo[3,3,0]octan-3-one, IR: 3600, 1770, 1590, 1495, 975 cm$^{-1}$. Melting point: 111°.

(b)

(1S,5R,6R,7R)-6-[(E)-3,3-Ethylenedioxy-4-(2-naphthyloxy)-1-butenyl]-7-(tetrahydropyran-2-yloxy)-2-oxabicyclo-[3,3,0]octan-3-one Formula VII: D = —CH$_2$—; E = —O—; $R_4$ = 2-naphthyl 190 mg. of (1S,5R,6R,7R)-6-[(E)-3,3-ethylenedioxy-4-(2-naphthyloxy)-1-butenyl]-7-hydroxy-2-oxabicyclo[3,3,0]octan-3-one (prepared according to Example 5[a]), 0.2 ml. of freshly distilled dihydropyran, and 1.4 mg. of p-toluenesulfonic acid in 5 ml. of absolute methylene chloride were stirred for 30 minutes at ice bath temperature under argon. After dilution with methylene chloride, the mixture was shaken successively with sodium bicarbonate solution and water, dried over magnesium sulfate, and evaporated under vacuum. The residue was recrystallized from diisopropyl ether/methylene chloride, thus obtaining 204 mg. of the title compound as colorless crystals, m.p. 113°. IR: 1770, 1630, 1600, 975 cm$^{-1}$.

Analogously, the following tetrahydropyranyl ethers are produced from the corresponding alcohols:

(1S,5R,6R,7R)-6-[(E)-3,3-ethylenedioxy-4-phenoxy-1-butenyl]-7-(tetrahydropyran-2-yloxy)-2-oxabicyclo[3,3,0]octan-3-one IR: 1770, 1590, 1500, 975 cm$^{-1}$.

(1S,5R,6R,7R)-6-[(E)-3,3-ethylenedioxy-4-(4-fluorophenoxy)-1-butenyl]-7-(tetrahydropyran-2-yloxy)-2-oxabicyclo[3,3,0]octan-3-one, IR: 1770, 1595, 1500, 970 cm$^{-1}$.

(1S,5R,6R,7R)-6-[(E)-3,3-ethylenedioxy-4-(4-chlorophenoxy)-1-butenyl]-7-(tetrahydropyran-2-yloxy)-2-oxabicyclo[3,3,0]octan-3-one, IR: 1770, 1590, 1500, 975 cm$^{-1}$.

(c)
(2RS,3aR,4R,5R,6aS)-4-[(E)-3,3-Ethylenedioxy-4-(2-naphthyloxy)-1-butenyl]-5-(tetrahydropyran-2-yloxy)-perhydrocyclopenta[b]furan-2-ol Formula VIII: D = —CH$_2$—; E = —O—; R$_4$ = 2-naphthyl Under argon at −70°, 1.5 ml. of a 20% solution of diisobutylaluminum hydride was added to a solution, cooled to −60°, of 150 mg. of (1S,5R,6R,7R)-6-[(E)-3,3-ethylenedioxy-4-(2-naphthyloxy)-1-butenyl]-7-(tetrahydropyran-2-yloxy)-2-oxabicyclo[3,3,0]octan-3-one (prepared according to Example 5[b]) in 15 ml. of absolute toluene. After 30 minutes, the mixture was combined with 0.75 ml. of isopropanol and 0.75 ml. of water and agitated for 30 minutes at 0°, diluted with 150 ml. of methylene chloride, filtered off from the precipitated aluminum compound, and evaporated under vacuum, thus obtaining 146 mg. of the title compound as a colorless oil. IR: 3600, 1630, 1600, 970 cm$^{-1}$.

Analogously, the following lactols are prepared from the corresponding lactones:

(2RS,3aR,4R,5R,6aS)-4-[(E)-3,3-ethylenedioxy-4-phenoxy-1-butenyl]-5-(tetrahydropyran-2-yloxy)-perhydrocyclopenta[b]-furan-2-ol (2RS,3aR,4R,5R,6aS)-4-[(E)-3,3-ethylenedioxy-4-(4-fluorophenoxy)-1-butenyl]-5-(tetrahydropyran-2-yloxy)-perhydrocyclopenta[b]furan-2-ol (2RS,3aR,4R,5R,6aS)-4-[(E)-3,3-ethylenedioxy-4-(4-chlorophenoxy)-1-butenyl]-5-(tetrahydropyran-2-yloxy)-perhydrocyclopenta[b]furan-2-ol (d)
(5Z,13E)-(8R,9S,11R,12R)-9-Hydroxy-11-(tetrahydropyran-2-yloxy)-15,15-ethylenedioxy-16-(2-naphthyloxy)-17,18,19,20-tetranor-prostadienoic Acid Formula IX: R$_1$ = H; D = —CH$_2$—; E = —O—; R$_4$ = 2-naphthyl At 15°, 35.2 ml. of a solution of methanesulfinylmethylsodium in absolute dimethyl sulfoxide (produced by stirring 1.76 g. of 50% sodium hydride - mineral oil suspension for 1 hour at 70° with 35.2 ml. of dimethyl sulfoxide) was dropped to a solution of 8.8 g. of 4-carboxybutyltriphenylphosphonium bromide in 30 ml. of absolute dimethyl sulfoxide; the mixture was agitated for 30 minutes at room temperature. The red ylene solution was dropped at 15° to a solution of 1.80 g. of (2RS,3aR,4R,5R,6aS)-4-[(E)-3,3-ethylenedioxy-4-(2-naphthyloxy)-1-butenyl]-5-(tetrahydropyran-2-yloxy)-perhydrocyclopenta[b]furan-2-ol (produced according to Example 5[c]) in 30 ml. of absolute dimethyl sulfoxide. The mixture was stirred for 2 hours at 50°. After removing the solvent under vacuum (about 0.01 torr), the residue was dissolved in 80 ml. of water, extracted three times with ether, and the ether extract was discarded. The aqueous phase was adjusted to pH 4–5 with 10% citric acid solution and extracted four times with a mixture of ether/hexane (1 + 1). The organic phase was shaken with brine, dried with magnesium sulfate, and evaporated under vacuum, thus obtaining 1.94 g. of the title compound as a colorless oil. IR: 3600–3300, 1710, 1630, 1600, 970 cm$^{-1}$.

Analogously, the following prostadienoic acids are obtained from the corresponding lactols (prepared according to Example 5[c]):

(5Z,13E)-(8R,9S,11R,12R)-9-hydroxy-11-(tetrahydropyran-2-yloxy)-15,15-ethylenedioxy-16-phenoxy-17,18,19,20-tetranorprostadienoic acid, IR: 3600–3400, 1710, 1595, 1490, 970 cm$^{-1}$. (5Z,13E)-(8R,9S,11R,12R)-9-hydroxy-11-(tetrahydropyran-2-yloxy)-15,15-ethylenedioxy-16-(4-fluorophenoxy)-17,18,19,20-tetranor-prostadienoic acid, IR: 3600—3300, 1715, 1600, 975 cm$^{-1}$.

(5Z,13E)-(8R,9S,11R,12R)-9-hydroxy-11-(tetrahydropyran-2-yloxy)-15,15-ethylenedioxy-16-(4-chlorophenoxy)-17,18,19,20-tetranor-prostadienoic acid, IR: 3600–3400, 1710, 1600, 978 cm$^{-1}$.

(e)
(5Z,13E)-(8R,11R,12R)-9-Oxo-11-(tetrahydropyran-2-yloxy)-15,15-ethylenedioxy-16-(2-naphthyloxy)-17,18,19,20-tetranor-prostadienoic Acid Formula X: R$_1$ = H; D = —CH$_2$—; E = —O—; R$_4$ = 2-naphthyl 165 mg. of (5Z,13E)-(8R,9S,11R,12R)-9-hydroxy-11-(tetrahydropyran-2-yloxy)-15,15-ethylenedioxy-16-(2-naphthyloxy)-17,18,19,20-tetranor-prostadienoic acid (prepared according to Example 5[d]) was dissolved in 4 ml. of acetone and combined at −20° with 0.15 ml. of Jones reagent (J. Chem. Soc. 1953, 2555). After 15 minutes, the excess reagent was destroyed by the dropwise addition of 0.2 ml. of isopropanol, diluted with 20 ml. of water, and extracted three times with methylene chloride. The organic extract was shaken with brine, dried over magnesium sulfate, and concentrated under vacuum. Yield: 110 mg. of the title compound as an oil having a slightly yellow color. IR: 3600–3300, 1740, 1710, 1630, 1600, 970 cm$^{-1}$.

In an analogous manner, the following PG'E$_2$ derivatives are produced from the corresponding PG'F$_{2\alpha}$ derivatives (produced according to Example 5[d]):

(5Z,13E)-(8R,11R,12R)-9-oxo-11-(tetrahydropyran-2-yloxy)-15,15-ethylenedioxy-16-phenoxy-17,18,19,20-tetranor-prostadienoic acid (5Z,13E)-(8R,11R,12R)-9-oxo-11-(tetrahydropyran-2-yloxy)-15,15-ethylenedioxy-16-(4-fluorophenoxy)-17,18,19,20-tetranor-prostadienoic acid (5Z,13E)-(8R,11R,12R)-9-oxo-11-(tetrahydropyran-2-yloxy)-15,15-ethylenedioxy-16-(4-chlorophenoxy)-17,18,19,20-tetranor-prostadienoic acid (f)
(5Z,13E)-(8R,11R,12R)-11-Hydroxy-9-oxo-15,15-ethylenedioxy-16-(2-naphthyloxy)-17,18,19,20-tetranorprostadienoic Acid Formula I: R$_1$ = H; R$_2$ and R$_3$ = O; R$_4$ = 2-naphthyl; A = trans-CH=CH; B = cis-CH=CH; D = —CH$_2$—; E = —O—;

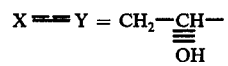

A mixture of 100 mg. of (5Z,13E)-(8R,11R,12R)-9-oxo-11-(tetrahydropyran-2-yloxy)-15,15-ethylenedioxy-16-(2-naphthyloxy)-17,18,19,20-tetranor-prostadienoic acid (prepared according to Example 5[e]) and 2 ml. of a solution of acetic acid/water/tetrahydrofuran (65/35/10) was agitated for 4 hours at room temperature, evaporated under vacuum, and the residue was chromatographed on silica gel; with chloroform/isopropanol (95+5), 51 mg. of the title compound was obtained as a colorless oil. IR: 3600–3400, 1740, 1710, 1630, 1600, 978 cm$^{-1}$.

Analogously, the following PG'E$_2$ derivatives are obtained from the corresponding tetrahydropyranyl ethers (produced according to Example 5[e]):

(5Z,13E)-(8R,11R,12R)-11-hydroxy-9-oxo-15,15-ethylenedioxy-16-phenoxy-17,18,19,20-tetranor-prostadienoic acid (5Z,13E)-(8R,11R,12R)-11-hydroxy-9-oxo-15,15-ethylenedioxy-16-(4-fluorophenoxy)-17,18,19,20-tetranor-prostadienoic acid (5Z,13E)-(8R,11R,12R)-11-hydroxy-9-oxo-15,15,-ethylenedioxy-16-(4-chlorophenoxy)-17,18,19,20-tetranor-prostadienoic acid

EXAMPLE 6

(5Z,13E)-(8R,9S,11R,12R)-9,11-Dihydroxy-15,15-ethylenedioxy-16-(2-naphthyloxy)-17,18,19,20-tetranor-prostadienoic Acid Formula Ia: A = trans-CH=CH; R$_1$ = H; D = —CH$_2$—; E = —O—; R$_4$ = 2-naphthyl At room temperature, 150 mg. of (5Z,13E)-(8R,9S,11R,12R)-9-hydroxy-11-(tetrahydropyran-2-yloxy)-15,15-ethylenedioxy-16-(2-naphthyloxy)-17,18,19,20-tetranor-prostadienoic acid (prepared according to Example 5[d]) was stirred in 3 ml. of a solution of acetic acid/water/tetrahydrofuran (65/35/10) for 4 hours; the mixture was concentrated by evaporation under vacuum, and chromatography on silica gel with chloroform/isopropanol (4 + 1) yielded 77 mg. of the title compound as a colorless oil; IR: 3600–3400, 1720, 1630, 1600, 978 cm$^{-1}$.

In an analogous manner, the following PG'F$_{2\alpha}$ derivatives are obtained from the corresponding tetrahydropyranyl ethers (produced according to Example 5[d]):

(5Z,13E)-(8R,9S,11R,12R)-9,11-dihydroxy-15,15-ethylenedioxy-16-phenoxy-17,18,19,20-tetranor-prostadienoic acid (5Z,13E)-(8R,9S,11R,12R)-9,11-dihydroxy-15,15-ethylenedioxy-16-(4-fluorophenoxy)-17,18,19,20-tetranor-prostadienoic acid (5Z,13E)-(8R,9S,11R,12R)-9,11-dihydroxy-15,15-ethylenedioxy-16-(4-chlorophenoxy)-17,18,19,20-tetranor-prostadienoic acid

EXAMPLE 7

(5Z,13E)-(8R,9S,11R,12R)-9,11-Dihydroxy-15,15-ethylenedioxy-16-phenoxy-17,18,19,20-tetranor-prostadienoic Acid Methyl Ester Formula Ia: A = trans-CH=CH; R$_1$ = methyl; D = —CH$_2$—; E = —O—; R$_4$ = phenyl An ethereal diazomethane solution was added dropwise to a solution of 150 mg. of (5Z,13E)-(8R,9S,11R,12R)-9,11-dihydroxy-15,15-ethylenedioxy-16-phenoxy-17,18,19,20-tetranor-prostadienoic acid (prepared according to Example 1 or 6) in 7 ml. of methylene chloride, until the yellow color remained. After three minutes, the mixture was evaporated under vacuum at room temperature, thus obtaining 150 mg. of the title compound as a colorless oil. IR: 3600, 1740, 1600, 1490, 970 cm$^{-1}$.

Analogously, the methyl esters of the following prostaglandin acids prepared according to Examples 1–6 are obtained:

(5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12)-9,11-dihydroxy-15,15-ethylenedioxy-20-ethyl-prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9-oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid and (5Z)-(8R,9S,12R)-9-hydroxy-11-oxo-15,15-ethylenedioxy-16-(2-naphthyloxy)-17,18,19,20-tetranor-prostenoic acid.

Replacing the diazomethane utilized in Example 7 by diazoethane, diazobutane, and diazodecane resulted in the corresponding ethyl, butyl, and decyl esters, respectively.

EXAMPLE 8

(5A,13E)-(8R,9S,11R,12R)-9,11-Dihydroxy-15,15-ethylenedioxy-16-phenoxy-17,18,19,20-tetranor-prostadienoic Acid p-Phenylphenacyl Ester Formula Ia: A = trans—CH=CH;

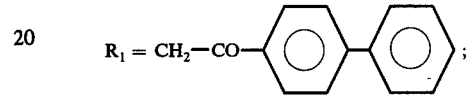

D = —CH$_2$—; E = —O—; R$_4$ = phenyl

Under argon, 77 mg. of (5Z,13E)-(8R,9S,11R,12R)-9,11-dihydroxy-15,15-ethylenedioxy-16-phenoxy-17,18,19,20-tetranor-prostadienoic acid (prepared according to Example 1 or 6) was agitated at room temperature for 12 hours with 53.6 mg. of p-phenylphenacyl bromide and 20 mg. of triethylamine in 3 ml. of absolute acetone. After dilution with water, the reaction mixture was extracted with ether, the ether extract was shaken with brine, dried over magnesium sulfate, and evaporated under vacuum. The residue was filtered over 5 g. of silica gel with ether/dioxane mixtures, thus obtaining 65 mg. of the title compound as a waxy mass.

IR: 3600–3400, 1740, 1700, 1600, 1495, 973 cm$^{-1}$.

Analogously, the p-phenylphenacyl esters of the following prostaglandin acids, prepared according to Examples 1 through 6, are obtained:

(5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12R)-9,11-dihydroxy-15,15-ethylenedioxy-20-ethyl-prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9-oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12R)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-(4-phenoxy)-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid and (5Z)-(8R,9S,12R)-9-hydroxy-11-oxo-15,15-ethylenedioxy-16-(2-naphthyloxy)-17,18,19,20-tetranor-prostenoic acid.

EXAMPLE 9

(5Z,13E)-(8R,9S,11R,12R)-9,11-Dihydroxy-15,15-ethylenedioxy-16-phenoxy-17,18,19,20-tetranor-prostadienoic Acid p-Chlorophenyl Ester At 0°, 100 mg. of (5Z,13E)-(8R,9S,11R,12R)-9,11-dihydroxy-15,15-ethylenedioxy-16-phenoxy-17,18,19,20-tetranor-prostadienoic acid (prepared according to Example 1 or 6), dissolved in 12 ml. of chloroform, was combined with 100 mg. of dicyclohexylcarbodiimide. After 1 hour, 1 g. of p-chlorophenol and 0.5 ml. of pyridine were added thereto and the mixture was stirred for 4 hours at room temperature. Then, the reaction mixture was filtered over silica gel with chloroform, thus obtaining 95 mg. of the title compound as a colorless, viscous oil.

IR: 3600, 1750, 1600, 1490, 1485, 970 cm$^{-1}$.

Analogously, the p-chlorophenyl esters of the following prostaglandin acids, prepared according to Examples 1–6, are obtained:

(5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12R)-9,11-dihydroxy-15,15-ethylenedioxy-20-ethyl-prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9-oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12R)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostanoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid and (5Z)-(8R,9S,12R)-9-hydroxy-11-oxo-15,15-ethylenedioxy-16-(2-naphthyloxy)-17,18,19,20-tetranor-prostenoic acid.

By replacing the p-chlorophenol employed in Example 9 by p-phenylphenol and p-fluorophenol, the corresponding p-phenylphenyl and p-fluorophenyl esters were produced.

EXAMPLE 10

Tris(hydroxymethyl)aminomethane Salt of (5Z,13E)-(8R,9S,11R,12R)-9,11-dihydroxy-15,15-ethylenedioxy-16-phenoxy-17,18,19,20-tetranor-prostadienoic Acid At 60°, a solution of 31 mg. of tris(hydroxymethyl)aminomethane in 0.1 ml. of water was added to a solution of 100 mg. of (5Z,13E)-(8R,9S,11R,12R)-9,11-dihydroxy-15,15-ethylenedioxy-16-phenoxy-17,18,19,20-tetranor-prostadienoic acid in 14 ml. of acetonitrile; the mixture was allowed to stand for 14 hours at room temperature, thus obtaining 72 mg. of the title compound as colorless crystals.

Analogously, the tris(hydroxymethyl)aminomethane salts of the following prostaglandin acids prepared according to Examples 1–6 are obtained:

(5Z,13E)-(8R,9S,11R,12R)-9,11-dihydroxy-15,15-ethylenedioxy-15-(4-chlorophenyl-16,17,18,19,20-pentanor-prostadienoic acid, (5Z,13E)-(8R,9S,11R,12R)-9,11-dihydroxy-15,15-ethylenedioxy-20-ethyl-prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9-oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12R)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid and (5Z)-(8R,9S,12R)-9-hydroxy-11-oxo-15,15-ethylenedioxy-16-(2-naphthyloxy)-17,18,19,20-tetranor-prostenoic acid.

EXAMPLE 11

(5Z,13E)-(8R,11R,12R)-11-Hydroxy-9-oxo-15,15-ethylenedioxy-16-phenoxy-17,18,19,20-tetranor-prostadienoic Acid Methyl Ester Formula I: $R_1$ = methyl; $R_2$ and $R_3$ = O; $R_4$ = phenyl; A = trans-CH=CH; B = cis-CH=CH; D = $CH_2$-; E = -O-;

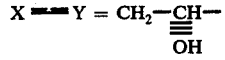

300 mg. of (5Z,13E)-(8R,9S,11R,12R)-9,11-dihydroxy-15,15-ethylenedioxy-16-phenoxy-17,18,19,20-tetranor-prostadienoic acid methyl ester (prepared according to Example 7) was stirred with 10 g. of pulverized silver carbonate in 60 ml. of toluene and heated for 5 hours under reflux. After cooling, the mixture was filtered and evaporated to dryness under vacuum. The residue was chromatographed on silica gel with ether/dioxane (95 + 5), thus obtaining 102 mg. of the title compound as an oil having a slightly yellow color.

IR: 3600, 1740, 1600, 1590, 1498, 978 cm$^{-1}$.

Analogously, the methyl esters of the PG E derivatives are obtained from the methyl esters of the PG F derivatives produced according to Example 7.

EXAMPLE 12

(13E)-(8R,9S,11R,12R)-9,11-Dihydroxy-15,15-ethylenedioxy-16-phenoxy-17,18,19,20-tetranor-prostenoic Acid Formula I: $R_1$ = $R_3$ = H; $R_2$ = OH; $R_4$ = phenyl; A = trans-CH=CH; B = —$CH_2$—$CH_2$—; D = —$CH_2$—; E = —O—;

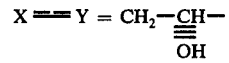

A mixture of 250 mg. of (5Z,13E)-(8R,9S,11R,12R)-15,15-ethylenedioxy-16-phenoxy-17,18,19,20-tetranor-prostadienoic acid (produced according to Example 1), 25 mg. of palladium on charcoal (10%), and 25 ml. of ethyl acetate was agitated for 2 hours at −20° under a hydrogen atmosphere. After filtration through a glass suction filter, the mixture was evaporated to dryness under vacuum, and the residue was filtered over silica gel with ether/dioxane (9 + 1), thus obtaining 180 mg. of the title compound as a colorless oil.

IR: 3600–3300, 1710, 1600, 1495, 975 cm$^{-1}$.

The NMR spectrum in CDCl$_3$ showed only two olefinic protons.

Analogously, the corresponding 5,6-dihydroprostaglandin derivatives can be prepared from the prostaglandin derivatives produced according to Examples 1, 2, 3, 4, 5, 6, 7, 8, 9, 11.

EXAMPLE 13

(5Z,13E)-(8R,9R,11R,12R)-9,11-Dihydroxy-15,15-ethylenedioxy-16-phenoxy-17,18,19,20-tetranor-prostadienoic Acid Formula I: $R_1$ = $R_2$ = H; $R_3$ = OH; $R_4$ = phenyl; A = trans-CH=CH; B = cis-CH=CH; D = —$Ch_2$—; E = —O—;

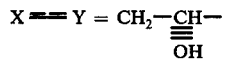

At 0°, a solution of 500 mg. of sodium borohydride in 60 ml. of methanol was dropped to a solution of 150 mg. of (5Z,13E)-(8R,11R,12R)-11-hydroxy-9-oxo-15,15-ethylenedioxy-16-phenoxy-17,18,19,20-tetranor-prostadienoic acid (prepared according to Example 3 or 5) in 15 ml. of methanol. The mixture was stirred for 1 hour at room temperature, concentrated under vacuum, diluted with water, the pH adjusted to 3–4 with dilute sulfuric acid, extracted with ether, the ether extract dried with magnesium sulfate, and evaporated under vacuum. By chromatography of the residue on 35 g. of silica gel, 43 mg. of the title compound was obtained with chloroform/isopropanol (95 + 5) as a colorless oil.

IR: 3600–3400, 1720, 1600, 1490, 970 cm$^{-1}$.

Analogously, the prostaglandin derivatives of the E series described in the above examples can be converted into the corresponding compounds with a 9 β-hydroxy group (9R configuration). Thus, the following compounds are obtained:

(5Z,13E)-(8R,9R,11R,12R)-9,11-dihydroxy-15,15-ethylenedioxy-15-(4-chlorophenyl)-16,17,18,19,20-pentanor-prostadienoic acid, (5Z,13E)-(8R,9R,11R,12R)-9,11-dihydroxy-15,15-ethylenedioxy-20-ethyl-prostadienoic acid, (5Z,13E)-(8R,9R,11R,12R)-9,11-dihydroxy-15,15-ethylenedioxy-16-n-propoxy-17,18,19,20-tetranor-prostadienoic acid, (5Z,13E)-(8R,9R,11R,12R)-9,11-dihydroxy-15,15-ethylenedioxy-19-oxa-prostadienoic acid, (5Z,13E)-(8R,9R,11R,12R)-9,11-dihydroxy-15,15-ethylenedioxy-17-phenyl-18,19,20-trinor-prostadienoic acid, (5Z,13E)-(8R,9R,11R,12R)-9,11-dihydroxy-15,15-ethylenedioxy-16-(4-fluorophenoxy)-17,18,19,20-tetranor-prostadienoic acid, (5Z,13E)-(8R,9R,11R,12R)-9,11-dihydroxy-15,15-ethylenedioxy-16-(4-chlorophenoxy)-17,18,19,20-tetranor-prostadienoic acid, (5Z,13E)-(8R,9R,11R,12R)-9,11-dihydroxy-15,15-ethylenedioxy-16-(2-naphthyloxy)-17,18,19,20-tetranor-prostadienoic acid, (5Z,13E)-(8R,9R,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9R,11R,12R)-9,11-dihydroxy-15,15-ethylenedioxy-15-(4-biphenylyl)-16,17,18,19,20-pentanor-prostadienoic acid, (5Z)-(8R,9R,11R,12R)-9,11-dihydroxy-15,15-ethylenedioxy-15-(4-chlorophenyl)-16,17,18,19,20-pentanor-prostenoic acid, (5Z)-(8R,9R,11R,12R)-9,11-dihydroxy-15,15-ethylenedioxy-17-phenyl-18,19,20-trinor-prostenoic acid, (5Z)-(8R,9R,11R,12R)-9,11-dihydroxy-15,15-ethylenedioxy-16-(4-fluorophenoxy)-17,18,19,20-tetranor-prostenoic acid, (5Z)-(8R,9R,11R,12R)-9,11-dihydroxy-15,15-ethylenedioxy-16-(4-chlorophenoxy)-17,18,19,20-tetranor-prostenoic acid, (5Z)-(8R,9R,11R,12R)-9,11-dihydroxy-15,15-ethylenedioxy-16-(2-naphthyloxy)-17,18,19,20-tetranor-prostenoic acid and (5Z)-(8R,9R,11R,12R)-9,11-dihydroxy-15,15-ethylenedioxy-16-phenoxy-17,18,19,20-tetranor-prostenoic acid.

Example 14

(5Z,10Z,13E)-(8R,12R)-9-Oxo-15,15-ethylenedioxy-16-phenoxy-17,18,19,20-tetranor-prostatrienoic Acid Methyl Ester Formula I: $R_1$ = methyl; $R_2$ and $R_3$ = O; $R_4$ = phenyl; A = trans-CH=CH; B = cis-CH=CH; D = —CH$_2$—; E = —O—; X===Y = CH=CH A mixture of 240 mg. of (5Z,13E)-(8R,11R,12R)-11-hydroxy-9-oxo-15,15-ethylenedioxy-16-phenoxy-17,18,19,20-tetranor-prostadienoic acid methyl ester (prepared according to Example 7), 700 mg. of dicyclohexylcarbodiimide, 80 mg. of copper(II) chloride dihydrate, 100 ml. of ether, and 4 mg. of pyridine was stirred for 12 hours at room temperature. Another 700 mg. of dicyclohexylcarbodiimide was added thereto, and the mixture was stirred for another 32 hours at room temperature. Then, the mixture was filtered and evaporated to dryness under vacuum. The residue was chromatographed on 30 g. of silica gel, eluted with either with the addition of 1-3% dioxane, and the title compound (130 mg.) was thus obtained as a colorless oil.

IR: 1740, 1700, 1600, 1495, 980 cm$^{-1}$.

Analogously, the following compounds are obtained from the corresponding 9-keto-11-hydroxyprostaglandins (prepared as described in Example 7):

(5Z,10Z,13E)-(8R,12R)-9-oxo-15,15-ethylenedioxy-15-(4-chlorophenyl-16,17,18,19 20-pentanor-prostatrienoic acid methyl ester (5Z,10Z,13E)-(8R,12R)-9-oxo-15,15-ethylenedioxy-16-(4-fluorophenoxy)-17,18,19,20-tetranor-prostatrienoic acid methyl ester (5Z,10Z,13E)-(8R,12R)-9-oxo-15,15-ethylenedioxy-16-(4-chlorophenoxy)-17,18,19,20-tetranor-prostatrienoic acid methyl ester

EXAMPLE 15

(5Z,13E)-(8R,9S,11R,12R)-9,11-Dihydroxy-15,15-ethylenedioxy-15-(4-chlorophenyl)-16,17,18,19,20-pentanor-prostadienoic Acid (4-Biphenylyl) Ester At 0°, 100 mg. of (5Z,13E)-(8R,9S,11R,12R)-9,11-dihydroxy-15,15-ethylenedioxy-15-(4-chlorophenyl)-16,17,18,19,-20-pentanor-prostadienoic acid (produced according to Example 1) dissolved in 10 ml. of chloroform was combined with 100 mg. of dicyclohexylcarbodiimide. After one hour, 1 g. of p-phenylphenol and 0.5 ml. of pyridine were added thereto, and the mixture was agitated at room temperature for 4 hours and then filtered with chloroform over silica gel. Yield: 60 mg. of the title compound as a colorless, viscous oil.

IR (in chloroform): 3600, 3000, 2940, 2895, 1750, 1600, 1483, 975, 835 cm$^{-1}$.

NMR (in DMSO-d$_6$) δ : 7.1 – 7.8 (13H,m); 5.25 – 5.7 (4H,m); 5.60 (1H,d,J=6Hz); 5.40 (1H,d,J=6Hz); 3.75–4.10 (6H,m).

EXAMPLE 16

(5Z,13E)-(8R,9S,11R,12R)-9,11-Dihydroxy-15,15-ethylenedioxy-20-ethyl-prostadienoic Acid (4-Biphenylyl) Ester At 0°, 300 mg. of (5Z,13E)-(8R,9S,11R,12R)-9,11-dihydroxy-15,15-ethylenedioxy-20-ethyl-prostadienoic acid (produced according to Example 1) dissolved in 15 ml. of chloroform was combined with 300 mg. of dicyclohexylcarbodiimide. After one hour, 3 g. of p-phenylphenol and 1.5 ml. of pyridine were added to the mixture and the latter stirred for 4 hours at room temperature. The mixture was then filtered with chloroform over silica gel, thus obtaining 150 mg. of the title compound as colorless crystals; m.p. 98°–99°.

EXAMPLE 17

(5Z,13E)-(8R,9S,11R,12R)-9,11-Dihydroxy-15,15-ethylenedioxy-16-(p-chlorophenyloxy)-17,18,19,20-tetranor-prostadienoic Acid (4-Biphenylyl) Ester At 0°, 100 mg. of (5Z,13E)-(8R,9S,11R,12R)-9,11-dihydroxy-15,15-ethylenedioxy-16-(p-chlorophenyloxy)-17,18,19,20-tetranor-prostadienoic acid (produced according to Example 1) dissolved in 10 ml. of chloroform was combined with 100 mg. of dicyclohexylcarbodiimide. After one hour, 1 g. of p-phenylphenol and 0.5 ml. of pyridine were added thereto, and the mixture was stirred for 4 hours at room temperature and filtered with chloroform over silica gel. After another purification by preparative layer chromatography on silica gel plates with ether/dioxane (9 + 1), 49 mg. of the title compound was obtained as a colorless oil.

IR: 3600, 3000, 2955, 2890, 1750, 1600, 1580, 1490, 978, 874, 825 cm$^{-1}$.

EXAMPLE 18

(a)

(1S,5R,6R,7R)-6-[(E)-3,3-Ethylenedioxy-4-(3-trifluoromethylphenyloxy)-1-butenyl]-7-benzoyloxy-2-oxabicyclo-[3,3,0]octan-3-one Formula III: A = trans-CH=CH; D = —CH$_2$—; E = —O—;

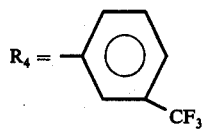

Ac = benzoyl

With the use of water trap, 1.85 g. of (1S,5R,6R,-7R)-6-[(E)-3-oxo-4-(3-trifluoromethylphenyloxy)-1-butenyl]-7-benzoyloxy-2-oxabicyclo[3,3,0]octan-3-one (prepared analogously to DOS 2,223,365) was refluxed for 16 hours in 70 ml. of benzene with 3.3 ml. of ethylene glycol and 21 mg. of p-toluenesulfonic acid. After cooling, the mixture was diluted with ether, shaken successively with sodium bicarbonate solution and water, dried over magnesium sulfate, and evaporated to dryness under vacuum. The oily residue was purified by column chromatography on silica gel. With ether/pentane (8 + 2), 1.6 g. of the title compound was eluted as a colorless oil.

IR (in chloroform): 2960, 1770, 1715, 1600, 1593, 1490, 1450, 976, 898 cm$^{-1}$.

NMR (CDCl$_3$) δ : 7.95 (2H,dd,J=8+2Hz); 7.0 – 7.6 (7H,m); 5.95(1H,dd,J=16+7Hz); 5.72 (1H,d,J=16Hz); 4.95 – 5.4 (2H,m); 3.9 –4.1 (6H,m)

(b)
(2RS,3aR,4R,5R,6aS)-4-[(E)-3,3-Ethylenedioxy-4-(3-trifluoromethylphenyloxy)-1-butenyl]-2,5-dihydroxyperhydrocyclopenta[b]furan Formula IV: A = trans-CH=CH; D = —CH$_2$—; E = —O—;

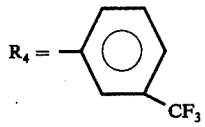

Under argon at −60°, 10 ml. of a 20% solution of diisobutylaluminum hydride in toluene was added dropwise to a solution of 1.54 g. of the compound produced according to (a) in 55 ml. of toluene; the mixture was stirred for 30 minutes at −60°. The reaction was terminated by the dropwise addition of isopropanol; then the mixture was combined with 5 ml. of water, allowed to warm to room temperature, agitated for 30 minutes at room temperature, filtered, and evaporated under vacuum. Filtering of the residue over silica gel yielded, with ether, 1.07 g. of the title compound as a colorless oil.

IR: 3600, 3300, 2960, 1593, 1490, 1450, 976 cm$^{-1}$.

(c)
(5Z,13E)-(8R,9S,11R,12R)-9,11-Dihydroxy-15,15-ethylenedioxy-16-(3-trifluoromethylphenyloxy)-17,18,19,20-tetranor-prostadienoic Acid Formula Ia: A = trans-CH=CH; R$_1$ = H; D = —CH$_2$—; E = —O—;

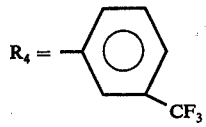

A solution of 5.73 g. of 4-carboxybutyltriphenylphosphonium bromide in 24 ml. of absolute DMSO was combined at 15° dropwise with 23.2 ml. of a solution of methanesulfinylmethyl-sodium in absolute DMSO (produced from 1.16 g. of 50% sodium hydride suspension in mineral oil in 24 ml. of DMSO and heating to 70° over one hour). The mixture was stirred for 30 minutes at room temperature. The red ylene solution was added dropwise at 15° to a solution of 1.07 g. of the compound prepared according to (b) in 12 ml. of DMSO and agitated for 2 hours at 50°. After the solvent had been removed by evaporation under vacuum, the residue was mixed with 50 ml. of water, extracted three times with respectively 600 ml. of ether, and the ether extract was discarded. The aqueous phase was adjusted to pH 4–5 with 10% citric acid solution and extracted four times with respectively 80 ml. of a mixture of ether/hexane (2 + 1). The organic phase was shaken with brine, dried with magnesium sulfate, and evaporated under vacuum. After chromatography of the residue on silica gel, 0.95 g. of the title compound was obtained with chloroform/isopropanol (5 + 1) in the form of a colorless oil.

IR: 3600–3400, 1715, 1595, 1490, 978 cm$^{-1}$.

EXAMPLE 19

(5Z,13E)-(8R,9S,11R,12R)-9,11-Dihydroxy-15,15-ethylenedioxy-16-(3-trifluoromethylphenyloxy)-17,18,19,20-tetranor-prostadienoic Acid Methyl Ester At 0°, 15 ml. of an ethereal diazomethane solution was added dropwise to a solution of 1.1 g. of (5Z,13E)-(8R,9S,-11R,12R)-9,11-dihydroxy-15,15-ethylenedioxy-16-(3-trifluoromethylphenyloxy)-17,18,19,20-tetranor-prostadienoic acid (prepared according to Example 18) in 50 ml. of methylene chloride ("Organikum" p. 528, publishers "Verlag der Wissenschaften, Berlin"). After 5 minutes, the mixture was evaporated under vacuum, and filtration over silica gel with ether/dioxane (9 + 1) yielded 1.05 g. of the title compound as a colorless oil.

NMR (CDCl$_3$) δ : 7.05 – 7.4 (4H,m); 5.89 (1H,dd,J=16+8 Hz); 5.60 (1H,d,J=16 Hz); 5.25 – 5.45 (2H,m); 3.85 – 4.26 (10H,m); 3.65 (3H,s).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostanoic acid derivative of the formula

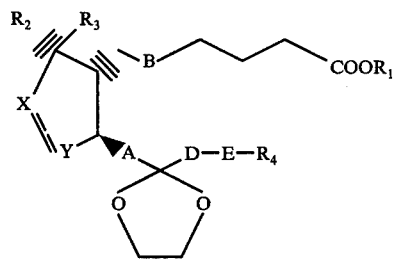

wherein R$_1$ is a hydrogen atom, alkyl of 1-10 carbon atoms, unsubstituted aryl, aryl substituted by 1-3 halogen atoms, one phenyl group, 1-3 alkyl groups of respectively 1-4 carbon atoms or one chloromethyl, fluoromethyl, trifluoromethyl, carboxyl or hydroxy group, or —CH₂—U—V wherein U is a direct bond, carbonyl, or carbonyloxy and V is phenyl or phenyl substituted by at least one of phenyl, alkoxy of 1-2 carbon atoms or a halogen atom; one of R₂ and R₃ is hydroxy and the other is a hydrogen atom or R₂ and R₃ collectively are an oxygen atom; A is —CH₂—CH₂— or a trans CH=CH; B is —CH₂—CH₂— or cis—CH=CH; D and E collectively are a direct bond, or D is alkylene of 1-5 carbon atoms and E is an oxygen or sulfur atom; R₄ is benzodioxol-2-yl, aryl or arylalkyl wherein alkyl is of 1-5 carbon atoms and aryl is unsubstituted or substituted as defined hereinabove, or when E is an oxygen or sulfur atom, also alkyl of 1-10 carbon atoms;

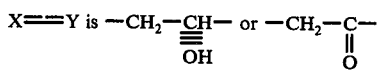

when one of R₂ and R₃ is a hydroxy group and the other is a hydrogen atom or

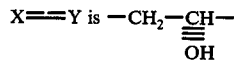

or —CH=CH when R₂ and R₃ collectively are an oxygen atom; and when R₁ is a hydrogen atom, the physiologically acceptable salts thereof with bases.

2. (5Z,13E)-(8R,9S,11R,12R)-9,11-Dihydroxy-15,15-ethylenedioxy-16-phenoxy-17,18,19,20-tetranor-prostadienoic acid, a compound of claim 1.

3. (5Z,13E)-(8R,9S,11R,12R)-9,11-Dihydroxy-15,15-ethylenedioxy-15-(4-chlorophenyl)-16,17,18,19,20-pentanor-prostadienoic acid, a compound of claim 1.

4. (5Z,13E)-(8R,9S,11R,12R)-9,11-Dihydroxy-15,15-ethylenedioxy-20-ethyl-prostadienoic acid, a compound of claim 1.

5. (5Z,13E)-(8R,9S,11R,12R)-9,11-Dihydroxy-15,15-ethylenedioxy-16-n-propoxy-17,18,19,20-tetranor-prostadienoic acid, a compound of claim 1.

6. (5Z,13E)-(8R,9S,11R,12R)-9,11-Dihydroxy-15,15-ethylenedioxy-19-oxa-prostadienoic acid, a compound of claim 1.

7. (5Z,13E)-(8R,9S,11R,12R)-9,11-Dihydroxy-15,15-ethylenedioxy-17-phenyl-18,19,20-trinor-prostadienoic acid, a compound of claim 1.

8. (5Z,13E)-(8R,9S,11R,12R)-9,11-Dihydroxy-15,15-ethylenedioxy-16-(4-fluorophenoxy)-17,18,19,20-tetranor-prostadienoic acid, a compound of claim 1.

9. (5Z,13E)-(8R,9S,11R,12R)-9,11-Dihydroxy-15,15-ethylenedioxy-16-(4-chlorophenoxy)-17,18,19,20-tetranor-prostadienoic acid, a compound of claim 1.

10. (5Z,13E)-(8R,9S,11R,12R)-9,11-Dihydroxy-15,15-ethylenedioxy-16-(2-naphthyloxy)-17,18,19,20-tetranor-prostadienoic acid, a compound of claim 1.

11. (5Z,13E)-(8R,9S,11R,12R)-9,11-Dihydroxy-15,15-ethylenedioxy-15-(1,3-dioxa-2-indanyl)-16,17,18,19,20-pentanor-prostadienoic acid, a compound of claim 1.

12. (5Z,13E)-(8R,9S,11R,12R)-9,11-Dihydroxy-15,15-ethylenedioxy-15-(4-biphenyl)-16,17,18,19,20-pentanor-prostadienoic acid, a compound of claim 1.

13. (5Z)-(8R,9S,11R,12R)-9,11-Dihydroxy-15,15-ethylenedioxy-16-phenoxy-17,18,19,20-tetranor-prostenoic acid, a compound of claim 1.

14. (5Z)-(8R,9S,11R,12R)-9,11-Dihydroxy-15,15-ethylenedioxy-15-(4-chlorophenyl)-16,17,18,19,20-pentanor-prostenoic acid, a compound of claim 1.

15. (5Z)-(8R,9S,11R,12R)-9,11-Dihydroxy-15,15-ethylenedioxy-17-phenyl-18,19,20-trinor-prostenoic acid, a compound of claim 1.

16. (5Z)-(8R,9S,11R,12R)-9,11-Dihydroxy-15,15-ethylenedioxy-16-(4-fluorophenoxy)-17,18,19,20-tetranor-prostenoic acid, a compound of claim 1.

17. (5Z)-(8R,9S,11R,12R)-9,11-Dihydroxy-15,15-ethylenedioxy-16-(4-chlorophenoxy)-17,18,19,20-tetranor-prostenoic acid, a compound of claim 1.

18. (5Z)-(8R,9S,11R,12R)-9,11-Dihydroxy-15,15-ethylenedioxy-16-(2-naphthyloxy)-17,18,19,20-tetranor-prostenoic acid, a compound of claim 1.

19. (5Z,13E)-(8R,11R,12R)-11-Hydroxy-9-oxo-15,15-ethylenedioxy-16-phenoxy-17,18,19,20-tetranor-prostadienoic acid, a compound of claim 1.

20. (5Z,13E)-(8R,11R,12R)-11-Hydroxy-9-oxo-15,15-ethylenedioxy-15-(4-chlorophenyl)-16,17,18,19,20-pentanor-prostadienoic acid, a compound of claim 1.

21. (5Z,13E)-(8R,11R,12R)-11-Hydroxy-9-oxo-15,15-ethylenedioxy-20-ethyl-prostadienoic acid, a compound of claim 1.

22. (5Z,13E)-(8R,11R,12R)-11-Hydroxy-9-oxo-15,15-ethylenedioxy-16-n-propoxy-17,18,19,20-tetranor-prostadienoic acid, a compound of claim 1.

23. (5Z,13E)-(8R,11R,12R)-11-Hydroxy-9-oxo-15,15-ethylenedioxy-19-oxa-prostadienoic acid, a compound of claim 1.

24. (5Z,13E)-(8R,11R,12R)-11-Hydroxy-9-oxo-15,15-ethylenedioxy-17-phenyl-18,19,20-trinor-prostadienoic acid, a compound of claim 1.

25. (5Z,13E)-(8R,11R,12R)-11-Hydroxy-9-oxo-15,15-ethylenedioxy-16-(4-fluorophenoxy)-17,18,19,20-tetranor-prostadienoic acid, a compound of claim 1.

26. (5Z,13E)-(8R,11R,12R)-11-Hydroxy-9-oxo-15,15-ethylenedioxy-16-(4-chlorophenoxy)-17,18,19,20-tetranor-prostadienoic acid, a compound of claim 1.

27. (5Z,13E)-(8R,11R,12R)-11-Hydroxy-9-oxo-15,15-ethylenedioxy-16-(2-naphthyloxy)-17,18,19,20-tetranor-prostadienoic acid, a compound of claim 1.

28. (5Z,13E)-(8R,11R,12R)-11-Hydroxy-9-oxo-15,15-ethylenedioxy-15-(1,3-dioxa-2-indanyl)-16,17,18,19,20-pentanor-prostadienoic acid, a compound of claim 1.

29. (5Z,13E)-(8R,11R,12R)-11-Hydroxy-9-oxo-15,15-ethylenedioxy-15-(4-biphenylyl)-16,17,18,19,20-pentanor-prostadienoic acid, a compound of claim 1.

30. (5Z)-(8R,11R,12R)-11-Hydroxy-9-oxo-15,15-ethylenedioxy-16-phenoxy-17,18,19,20-tetranor-prostenoic acid, a compound of claim 1.

31. (5Z)-(8R,11R,12R)-11-Hydroxy-9-oxo-15,15-ethylenedioxy-15-(4-chlorophenyl)-16,17,18,19,20-pentanor-prostenoic acid, a compound of claim 1.

32. (5Z)-(8R,11R,12R)-11-Hydroxy-9-oxo-15,15-ethylenedioxy-17-phenyl-18,19,20-trinor-prostenoic acid, a compound of claim 1.

33. (5Z)-(8R,11R,12R)-11-Hydroxy-9-oxo-15,15-ethylenedioxy-16-(4-fluorophenoxy)-17,18,19,20-tetranor-prostenoic acid, a compound of claim 1.

34. (5Z)-(8R,11R,12R)-11-Hydroxy-9-oxo-15,15-ethylenedioxy-16-(4-chlorophenoxy)-17,18,19,20-tetranor-prostenoic acid, a compound of claim 1.

35. (5Z)-(8R,11R,12R)-11-Hydroxy-9-oxo-15,15-ethylenedioxy-16-(2-naphthyloxy)-17,18,19,20-tetranor-prostenoic acid, a compound of claim 1.

36. (5Z,13E)-(8R,9S,12R)-9-Hydroxy-11-oxo-15,15-ethylenedioxy-16-phenoxy-17,18,19,20-tetranor-prostadienoic acid, a compound of claim 1.

37. (5Z,13E)-(8R,9S,12R)-9-Hydroxy-11-oxo-15,15-ethylenedioxy-15-(4-chlorophenyl)-16,17,18,19,20-pentanor-prostadienoic acid, a compound of claim 1.

38. (5Z,13E)-(8R,9S,12R)-9-Hydroxy-11-oxo-15,15-ethylenedioxy-20-ethyl-prostadienoic acid, a compound of claim 1.

39. (5Z,13E)-(8R,9S,12R)-9-Hydroxy-11-oxo-15,15-ethylenedioxy-16-n-propoxy-17,18,19,20-tetranor-prostadienoic acid, a compound of claim 1.

40. (5Z,13E)-(8R,9S,12R)-9-Hydroxy-11-oxo-15,15-ethylenedioxy-19-oxa-prostadienoic acid, a compound of claim 1.

41. (5Z,13E)-(8R,9S,12R)-9-Hydroxy-11-oxo-15,15-ethylenedioxy-17-phenyl-18,19,20-trinor-prostadienoic acid, a compound of claim 1.

42. (5Z,13E)-(8R,9S,12R)-9-Hydroxy-11-oxo-15,15-ethylenedioxy-16-(4-fluorophenoxy)-17,18,19,20-tetranor-prostadienoic acid, a compound of claim 1.

43. (5Z,13E)-(8R,9S,12R)-9-Hydroxy-11-oxo-15,15-ethylenedioxy-16-(4-chlorophenoxy)-17,18,19,20-tetranor-prostadienoic acid, a compound of claim 1.

44. (5Z,13E)-(8R,9S,12R)-9-Hydroxy-11-oxo-15,15-ethylenedioxy-16-(2-naphthyloxy)-17,18,19,20-tetranor-prostadienoic acid, a compound of claim 1.

45. (5Z,13E)-(8R,9S,12R)-9-Hydroxy-11-oxo-15,15-ethylenedioxy-15-(1,3-dioxa-2-indanyl)-16,17,18,19,20-pentanor-prostadienoic acid, a compound of claim 1.

46. (5Z,13E)-(8R,9S,12R)-9-Hydroxy-11-oxo-15,15-ethylenedioxy-15-(4-biphenylyl)-16,17,18,19,20-pentanor-prostadienoic acid, a compound of claim 1.

47. (5Z)-(8R,9S,12R)-9-Hydroxy-11-oxo-15,15-ethylenedioxy-16-phenoxy-17,18,19,20-tetranor-prostenoic acid, a compound of claim 1.

48. (5Z)-(8R,9S,12R)-9-Hydroxy-11-oxo-15,15-ethylenedioxy-15-(4-chlorophenyl)-16,17,18,19,20-pentanor-prostenoic acid, a compound of claim 1.

49. (5Z)-(8R,9S,12R)-9-Hydroxy-11-oxo-15,15-ethylenedioxy-17-phenyl-18,19,20-trinor-prostenoic acid, a compound of claim 1.

50. (5Z)-(8R,9S,12R)-9-Hydroxy-11-oxo-15,15-ethylenedioxy-16-(4-fluorophenoxy)-17,18,19,20-tetranor-prostenoic acid, a compound of claim 1.

51. (5Z)-(8R,9S,12R)-9-Hydroxy-11-oxo-15,15-ethylenedioxy-16-(4-chlorophenoxy)-17,18,19,20-tetranor-prostenoic acid, a compound of claim 1.

52. (5Z)-(8R,9S,12R)-9-Hydroxy-11-oxo-15,15-ethylenedioxy-16-(2-naphthyloxy)-17,18,19,20-tetranor-prostenoic acid, a compound of claim 1.

53. (5Z,13E)-(8R,9S,11R,12R)-9,11-Dihydroxy-15,15-ethylenedioxy-16-phenoxy-17,18,19,20-tetranor-prostadienoic acid methyl ester, a compound of claim 1.

54. Compounds of claim 1 which are the methyl, ethyl, butyl and decyl esters of (5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12R)-9,11-dihydroxy-15,15-ethylenedioxy-20-ethyl prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-phenoxy-17,18,19,20-tetranor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9-oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12R)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid or (5Z)-(8R,9S,12R)-9-hydroxy-11-oxo-15,15-ethylenedioxy-16-(2-naphthyloxy)-17,18,19,20-tetranor-prostenoic acid.

55. The p-phenylphenacyl ester of (5Z,13E)-(8R,9S,11R,12R)-9,11-dihydroxy-15,15-ethylenedioxy-16-phenoxy-17,18,19,20-tetranor-prostadienoic acid, a compound of claim 1.

56. Compounds of claim 1 which are the p-phenylphenacyl esters of (5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12R)-9,11-dihydroxy-15,15-ethylenedioxy-20-ethyl-prostadienoic acid, (5Z,13E)-(8R,9S,11R, 12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R, 12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid, (5Z)-(8R,9S,11R,12R)-9,11-dihydroxy-15,15-ethylenedioxy-16-phenoxy-17,18,19,20-tetranor-prostenoic acid, (5Z,13E)-(8R,11R,12R)-11-hydroxy-9-oxo-15,15-ethylenedioxy-15-(4-chlorophenyl)-16,17,18,19,20-pentanor-prostadienoic acid, (5Z,13E)-(8R,11R,12R)-11-hydroxy-9oxo-15,15-ethylenedioxy-20-ethyl-prostadienoic acid, (5Z,13E)-(8R,11R,12R)-11-hydroxy-9-oxo-15,15-ethylenedioxy-16-n-propoxy-17,18,19,20-tetranor-prostadienoic acid, (5Z,13E)-(8R,11R,12R)-11-hydroxy-9-oxo-15,15-ethylenedioxy-19-oxa-prostadienoic acid, (5Z,13E)-(8R,11R,12R)-11-hydroxy-9-oxo-15,15-ethylenedioxy-17-phenyl-18,19,20-trinor-prostadienoic acid, (5Z,13E)-(8R,11R,12R)-11-hydroxy-9-oxo-15,15-ethylenedioxy-16-(4-fluorophenoxy)-17,18,19,20-tetranor-prostadienoic acid, (5Z,13E)-(8R,11R,12R)-11-hydroxy-9-oxo-15,15-ethylenedioxy-16-(4-chlorophenoxy)-17,18,19,20-tetranor-prostadienoic acid, (5Z,13E)-(8R,11R,12R)-11-hydroxy-9-oxo-15,15-ethylenedioxy-16-(2-naphthyloxy)-17,18,19,20-tetranor-prostadienoic acid, (5Z,13E)-(8R,11R,12R)-11-hydroxy-9-oxo-15,15-ethylenedioxy-15-(1,3-dioxa-2-indanyl)-16,17,18,19,20-pentanor-prostadienoic acid, (5Z,13E)-(8R,11R,12R)-11-hydroxy-9-oxo-15,15-ethylenedioxy-15-(4-biphenylyl)-16,17,18,19,20-pentanor-prostadienoic acid, (5Z,13E)-(8R,11R,12R)-11-hydroxy-9-oxo-15,15-ethylenedioxy-16-phenoxy-17,18,19,20-tetranor-prostadienoic acid, (5Z)-(8R,11R,12R)-11-hydroxy-9-oxo-15,15-ethylenedioxy-16-phenoxy-17,18,19,20-tetranor-prostenoic acid, (5Z)-(8R,11R,12R)-11-hydroxy-9-oxo-15,15-ethylenedioxy-15-(4-chlorophenyl)-16,17,18,19,20-pentanor-prostenoic acid, (5Z)-(8R,11R,12R)-11-hydroxy-9-oxo-15,15-ethylenedioxy-17-phenyl-18,19,20-trinor-prostenoic acid, (5Z)-(8R,11R,12R)-11-hydroxy-9-oxo-15,15-ethylenedioxy-16-(4-fluorophenoxy)-17,18,19,20-tetranor-prostenoic acid, (5Z)-(8R,11R,12R)-11-hydroxy-9-oxo-15,15-ethylenedioxy-16-(4-chlorophenoxy)-17,18,19,20-tetranor-prostenoic acid, (5Z)-(8R,11R,12R)-11-hydroxy-9-oxo-15,15-ethylenedioxy-16-(2-naphthyloxy)-17,18,19,20-tetranor-prostenoic acid, (5Z,13E)-(8R,9S,12R)-9-hydroxy-11-oxo-15,15-ethylenedioxy-16-phenoxy-17,18,19,20-tetranor-prostadienoic acid, (5Z,13E)-(8R,9S,12R)-9-hydroxy-11-oxo-15,15-ethylenedioxy-15-(4-chlorophenyl)-16,17,18,19,20-pentanor-prostadienoic acid, (5Z,13E)-(8R,9S,12R)-9-hydroxy-11-oxo-15,15-ethylenedioxy-20-ethyl-prostadienoic acid, (5Z,13E)-(8R,9S,12R)-9-hydroxy-11-oxo-15,15-ethylenedioxy-16-n-propoxy-17,18,19,20-tetranor-prostadienoic acid, (5Z,13E)-(8R,9S,12R)-9-hydroxy-11-oxo-15,15-ethylenedioxy-19-oxa-prostadienoic acid, (5Z,13E)-(8R,9S,12R)-9-hydroxy-11-oxo-15,15-ethylenedioxy-17-phenyl-18,19,20-trinor-prostadienoic acid, (5Z,13E)-(8R,9S,12R)-9-hydroxy-11-oxo-15,15-ethylenedioxy-16-(4-fluorophenoxy)-17,18,19,20-tetranor-prostadienoic acid, (5Z,13E)-(8R,9S,12R)-9-hydroxy-11-oxo-15,15-ethylenedioxy-16-(4-chlorophenoxy)-17,18,19,20-tetranor-prostadienoic acid, (5Z,13E)-(8R,9S,12R)-9-hydroxy-11-oxo-15,15-ethylenedioxy-16-(2-naphthyloxy)-17,18,19,20-tetranor-prostadienoic acid, (5Z,13E)-(8R,9S,12R)-9-hydroxy-11-oxo-15,15-ethylenedioxy-15-(1,3-dioxa-2-indanyl)-16,17,18,19,20-pentanor-prostadienoic acid, (5Z,13E)-(8R,9S,12R)-9-hydroxy-11-oxo-15,15-ethylenedioxy-15-(4-biphenylyl)-16,17,18,19,20-pentanor-prostadienoic acid, (5Z)-(8R,9S,12R)-9-hydroxy-11-oxo-15,15-ethylenedioxy-16-phenoxy-17,18,19,20-tetranor-prostenoic acid, (5Z)-(8R,9S,12R)-9-hydroxy-11-oxo-15,15-ethylenedioxy-15-(4-chlorophenyl)-16,17,18,19,20-pentanor-prostenoic acid, (5Z)-(8R,9S,12R)-9-hydroxy-11-oxo-15,15-ethylenedioxy-17-phenyl-18,19,20-trinor-prostenoic acid, (5Z)-(8R,9S,12R)-9-hydroxy-11-oxo-15,15-ethylenedioxy-16-(4-fluorophenoxy)-17,18,19,20-tetranor-prostenoic acid, (5Z)-(8R,9S,12R)-9-hydroxy-11-oxo-15,15-ethylenedioxy-16-(4-chlorophenoxy)-17,18,19,20-tetranor-prostenoic acid or (5Z)-(8R,9S,12R)-9-hydroxy-11-oxo-15,15-ethylenedioxy-16-(2-naphthyloxy)-17,18,19,20-tetranor-prostenoic acid.

57. A compound of claim 1, the p-chlorophenyl ester of (5Z,13E)-(8R,9S,11R,12R)-9,11-dihydroxy-15,15-ethylenedioxy-16-phenoxy-17,18,19,20-tetranor-prostadienoic acid.

58. Compounds of claim 1 which are the p-chlorophenyl, p-phenylphenyl, and p-fluorophenyl esters of (5Z,13E)-(8R,9S,11R,12R)-9,11-dihydroxy-15,15-ethylenedioxy-15-(4-chlorophenyl)-16,17,18,19,20-pentanor-prostadienoic acid, (5Z,13E)-(8R,9S,11R,12R)-9,11-dihydroxy-15,15-ethylenedioxy-20-ethyl-prostadienoic acid, (5Z,13E)-(8R,9S,11R,12R)-9,11-dihydroxy-15,15-ethylenedioxy-16-n-propoxy-17,18,19,20-tetranor-prostadienoic acid, (5Z,13E)-(8R,9S,11R,12R)-9,11-dihydroxy-15,15-ethylenedioxy-19-oxa-prostadienoic acid, (5Z,13E)-(8R,9S,11R,12R)-9,11-dihydroxy-15,15-ethylenedioxy-17-phenyl-18,19,20-trinor-prostadienoic acid, (5Z,13E)-(8R,9S,11R,12R)-9,11-dihydroxy-15,15-ethylenedioxy-16-phenoxy-17,18,19,20-tetranor-prostadienoic acid, (5Z,13E)-(8R,9S,11R,12R)-9,11-dihydroxy-15,15-ethylenedioxy-16-(4-fluorophenoxy)-17,18,19,20-tetranor-prostadienoic acid, (5Z,13E)-(8R,9S,11R,12R)-9,11-dihydroxy-15,15-ethylenedioxy-16-(4-chlorophenoxy)-17,18,19,20-tetranor-prostadienoic acid, (5Z,13E)-(8R,9S,11R,12R)-9,11-dihydroxy-15,15-ethylenedioxy-16-(2-naphthyloxy)-17,18,19,20-tetranor-prostadienoic acid, (5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid, (5Z)-(8R,9S,11R,12R)-9,11-dihydroxy-15,15-ethylenedioxy-15-(4-chlorophenyl)-16,17,18,19,20-pentanor-prostenoic acid, (5Z)-(8R,9S,11R,12R)-9,11-dihydroxy-15,15-ethylenedioxy-17-phenyl-18,19,20-trinor-prostenoic acid, (5Z)-(8R,9S,11R,12R)-9,11-dihydroxy-15,15-ethylenedioxy-16-(4-fluorophenoxy)-17,18,19,20-tetranor-prostenoic acid, (5Z)-(8R,9S,11R,12R)-9,11-dihydroxy-15,15-ethylenedioxy-16-(4-chlorophenoxy)-17,18,19,20-tetranor-prostenoic acid, (5Z)-(8R,9S,11R,12R)-9,11-dihydroxy-15,15-ethylenedioxy-16-(2-naphthyloxy)-17,18,19,20-tetranor-prostenoic acid,
(5Z)-(8R,9S,11R,12R)-9,11-dihydroxy-15,15-ethylenedioxy-16-phenoxy-17,18,19,20-tetranor-prostenoic acid,
(5Z,13E)-(8R,11R,12R)-11-hydroxy-9-oxo-15,15-ethylenedioxy-15-(4-chlorophenyl)-16,17,18,19,20-pentanor-prostadienoic acid,
(5Z,13E)-(8R,11R,12R)-11-hydroxy-9-oxo-15,15-ethylenedioxy-20-ethyl-prostadienoic acid,
(5Z,13E)-(8R,11R,12R)-11-hydroxy-9-oxo-15,15-ethylenedioxy-16-n-propoxy-17,18,19,20-tetranor-prostadienoic acid,
(5Z,13E)-(8R,11R,12R)-11-hydroxy-9-oxo-15,15-ethylenedioxy-19-oxa-prostadienoic acid,
(5Z,13E)-(8R,11R,12R)-11-hydroxy-9-oxo-15,15-ethylenedioxy-17-phenyl-18,19,20-trinor-prostadienoic acid,
(5Z,13E)-(8R,11R,12R)-11-hydroxy-9-oxo-15,15-ethylenedioxy-16-(4-fluorophenoxy)-17,18,19,20-tetranor-prostadienoic acid,
(5Z,13E)-(8R,11R,12R)-11-hydroxy-9-oxo-15,15-ethylenedioxy-16-(4-chlorophenoxy)-17,18,19,20-tetranor-prostadienoic acid,
(5Z,13E)-(8R,11R,12R)-11-hydroxy-9-oxo-15,15-ethylenedioxy-16-(2-naphthyloxy)-17,18,19,20-tetranor-prostadienoic acid,
(5Z,13E)-(8R,11R,12R)-11-hydroxy-9-oxo-15,15-ethylenedioxy-15-(1,3-dioxa-2-indanyl)-16,17,18,19,20-pentanor-prostadienoic acid,
(5Z,13E)-(8R,11R,12R)-11-hydroxy-9-oxo-15,15-ethylenedioxy-15-(4-biphenylyl)-16,17,18,19,20-pentanor-prostadienoic acid,
(5Z,13E)-(8R,11R,12R)-11-hydroxy-9-oxo-15,15-ethylenedioxy-16-phenoxy-17,18,19,20-tetranor-prostadienoic acid,
(5Z)-(8R,11R,12R)-11-hydroxy-9-oxo-15,15-ethylenedioxy-16-phenoxy-17,18,19,20-tetranor-prostenoic acid,
(5Z)-(8R,11R,12R)-11-hydroxy-9-oxo-15,15-ethylenedioxy-15-(4-chlorophenyl)-16,17,18,19,20-pentanor-prostenoic acid,
(5Z)-(8R,11R,12R)-11-hydroxy-9-oxo-15,15-ethylenedioxy-17-phenyl-18,19,20-trinor-prostenoic acid,
(5Z)-(8R,11R,12R)-11-hydroxy-9-oxo-15,15-ethylenedioxy-16-(4-fluorophenoxy)-17,18,19,20-tetranor-prostenoic acid,
(5Z)-(8R,11R,12R)-11-hydroxy-9-oxo-15,15-ethylenedioxy-16-(4-chlorophenoxy)-17,18,19,20-tetranor-prostenoic acid,
(5Z)-(8R,11R,12R)-11-hydroxy-9-oxo-15,15-ethylenedioxy-16-(2naphthyloxy)-17,18,19,20-tetranor-prostenoic acid,
(5Z,13E)-(8R,9S,12R)-9-hydroxy-11-oxo-15,15-ethylenedioxy-16-phenoxy-17,18,19,20-tetranor-prostadienoic acid,
(5Z,13E)-(8R,9S,12R)-9-hydroxy-11-oxo-15,15-ethylenedioxy-15-(4-chlorophenyl)-16,17,18,19,20-pentanor-prostadienoic acid,
(5Z,13E)-(8R,9S,12R)-9-hydroxy-11-oxo-15,15-ethylenedioxy-20-ethyl-prostadienoic acid,
(5Z,13E)-(8R,9S,12R)-9-hydroxy-11-oxo-15,15-ethylenedioxy-16-n-propoxy-17,18,19,20-tetranor-prostadienoic acid,
(5Z,13E)-(8R,9S,12R)-9-hydroxy-11-oxo-15,15-ethylenedioxy-19-oxa-prostadienoic acid,
(5Z,13E)-(8R,9S,12R)-9-hydroxy-11-oxo-15,15-ethylenedioxy-17-phenyl-18,19,20-trinor-prostadienoic acid,
(5Z,13E)-(8R,9S,12R)-9-hydroxy-11-oxo-15,15-ethylenedioxy-16-(4-fluorophenoxy)-17,18,19,20-tetranor-prostadienoic acid,
(5Z,13E)-(8R,9S,12R)-9-hydroxy-11-oxo-15,15-ethylenedioxy-16-(4-chlorophenoxy)-17,18,19,20-tetranor-prostadienoic acid,
(5Z,13E)-(8R,9S,12R)-9-hydroxy-11-oxo-15,15-ethylenedioxy-16-(2-naphthyloxy)-17,18,19,20-tetranor-prostadienoic acid,
(5Z,13E)-(8R,9S,12R)-9-hydroxy-11-oxo-15,15-ethylenedioxy-15-(1,3-dioxa-2-indanyl)-16,17,18,19,20-pentanor-prostadienoic acid,
(5Z,13E)-(8R,9S,12R)-9-hydroxy-11-oxo-15,15-ethylenedioxy-15-(4-biphenylyl)-16,17,18,19,20-pentanor-prostadienoic acid,
(5Z)-(8R,9S,12R)-9-hydroxy-11-oxo-15,15-ethylenedioxy-16-phenoxy-17,18,19,20-tetranor-prostenoic acid,
(5Z)-(8R,9S,12R)-9-hydroxy-11-oxo-15,15-ethylenedioxy-15-(4-chlorophenyl)-16,17,18,19,20-pentanor-prostenoic acid,
(5Z)-(8R,9S,12R)-9-hydroxy-11-oxo-15,15-ethylenedioxy-17-phenyl-18,19,20-trinor-prostenoic acid,
(5Z)-(8R,9S,12R)-9-hydroxy-11-oxo-15,15-ethylenedioxy-16-(4-fluorophenoxy)-17,18,19,20-tetranor-prostenoic acid,
(5Z)-(8R,9S,12R)-9-hydroxy-11-oxo-15,15-ethylenedioxy-16-(4-chlorophenoxy)-17,18,19,20-tetranor-prostenoic acid or
(5Z)-(8R,9S,12R)-9-hydroxy-11-oxo-15,15-ethylenedioxy-16-(2-naphthyloxy)-17,18,19,20-tetranor-prostenoic acid.

59. The tris(hydroxymethyl)aminomethane salt of (5Z,13E)-(8R,9S,11R,12R)-9,11-dihydroxy-15,15-ethylenedioxy-16-phenoxy-17,18,19,20-tetranor-prostadienoic acid, a compound of claim 1.

60. Compounds of claim 1 which are the tris(hydroxymethyl)aminomethane salt of
(5Z,13E)-(8R,9S,11R,12R)-9,11-dihydroxy-15,15-ethylenedioxy-15-(4-chlorophenyl)-16,17,18,19,20-pentanor-prostadienoic acid,
(5Z,13E)-(8R,9S,11R,12R)-9,11-dihydroxy-15,15-ethylenedioxy-20-ethyl-prostadienoic acid,
(5Z,13E)-(8R,9S,11R,12R)-9,11-dihydroxy-15,15-ethylenedioxy-16-n-propoxy-17,18,19,20-tetranor-prostadienoic acid,
(5Z,13E)-(8R,9S,11R,12R)-9,11-dihydroxy-15,15-ethylenedioxy-19-oxa-prostadienoic acid,
(5Z,13E)-(8R,9S,11R,12R)-9,11-dihydroxy-15,15-ethylenedioxy-17-phenyl-18,19,20-trinor-prostadienoic acid,
(5Z,13E)-(8R,9S,11R,12R)-9,11-dihydroxy-15,15-ethylenedioxy-16-(4-fluorophenoxy)-17,18,19,20-tetranor-prostadienoic acid,
(5Z,13E)-(8R,9S,11R,12R)-9,11-dihydroxy-15,15-ethylenedioxy-16-(4-chlorophenoxy)-17,18,19,20-tetranor-prostadienoic acid,
(5Z,13E)-(8R,9S,11R,12R)-9,11-dihydroxy-15,15-ethylenedioxy-16-(2-naphthyloxy)-17,18,19,20-tetranor-prostadienoic acid,
(5Z,13E)-(8R,9S,11R,12R)-9,11-dihydroxy-15,15-ethylenedioxy-15-(1,3-dioxa-2-indanyl)-16,17,18,19,20-pentanor-prostadienoic acid, (5Z,13E)-(8R,9S,11R,12R)-9,11-dihydroxy-15,15-ethylenedioxy-15-(4-biphenylyl)-16,17,18,19,20-pentanor-prostadienoic acid,
(5Z)-(8R,9S,11R,12R)-9,11-dihydroxy-15,15-ethylenedioxy-15-(4-chlorophenyl)-16,17,18,19,20-pentanor-prostenoic acid,
(5Z)-(8R,9S,11R,12R)-9,11-dihydroxy-15,15-ethylenedioxy-17-phenyl-18,19,20-trinor-prostenoic acid,
(5Z)-(8R,9S,11R,12R)-9,11-dihydroxy-15,15-ethylenedioxy-16-(4-fluorophenoxy)-17,18,19,20-tetranor-prostenoic acid,
(5Z)-(8R,9S,11R,12R)-9,11-dihydroxy-15,15-ethylenedioxy-16-(4-chlorophenoxy)-17,18,19,20-tetranor-prostenoic acid,
(5Z)-(8R,9S,11R,12R)-9,11-dihydroxy-15,15-ethylenedioxy-16-(2-naphthyloxy)-17,18,19,20-tetranor-prostenoic acid,
(5Z)-(8R,9S,11R,12R)-9,11-dihydroxy-15,15-ethylenedioxy-16-phenoxy-17,18,19,20-tetranor-prostenoic acid,
(5Z,13E)-(8R,11R,12R)-11-hydroxy-9-oxo-15,15-ethylenedioxy-15-(4-chlorophenyl)-16,17,18,19,20-pentanor-prostadienoic acid,
(5Z,13E)-(8R,11R,12R)-11-hydroxy-9-oxo-15,15-ethylenedioxy-20-ethyl-prostadienoic acid,
(5Z,13E)-(8R,11R,12R)-11-hydroxy-9-oxo-15,15-ethylenedioxy-16-n-propoxy-17,18,19,20-tetranor-prostadienoic acid,
(5Z,13E)-(8R,11R,12R)-11-hydroxy-9-oxo-15,15-ethylenedioxy-19-oxa-prostadienoic acid,
(5Z,13E)-(8R,11R,12R)-11-hydroxy-9-oxo-15,15-ethylenedioxy-17-phenyl-18,19,20-trinor-prostadienoic acid,
(5Z,13E)-(8R,11R,12R)-11-hydroxy-9-oxo-15,15-ethylenedioxy-16-(4-fluorophenoxy)-17,18,19,20-tetranor-prostadienoic acid,
(5Z,13E)-(8R,11R,12R)-11-hydroxy-9-oxo-15,15-ethylenedioxy-16-(4-chlorophenoxy)-17,18,19,20-tetranor-prostadienoic acid,
(5Z,13E)-(8R,11R,12R)-11-hydroxy-9-oxo-15,15-ethylenedioxy-16-(2-naphthyloxy)-17,18,19,20-tetranor-prostadienoic acid,
(5Z,13E)-(8R,11R,12R)-11-hydroxy-9-oxo-15,15-ethylenedioxy-15-(1,3-dioxa-2-indanyl)-16,17,18,19,20-pentanor-prostadienoic acid,
(5Z,13E)-(8R,11R,12R)-11-hydroxy-9-oxo-15,15-ethylenedioxy-15-(4-biphenylyl)-16,17,18,19,20-pentanor-prostadienoic acid,
(5Z,13E)-(8R,11R,12R)-11-hydroxy-9-oxo-15,15-ethylenedioxy-16-phenoxy-17,18,19,20-tetranor-prostadienoic acid,
(5Z)-(8R,11R,12R)-11-hydroxy-9-oxo-15,15-ethylenedioxy-16-phenoxy-17,18,19,20-tetranor-prostenoic acid,
(5Z)-(8R,11R,12R)-11-hydroxy-9-oxo-15,15-ethylenedioxy-15-(4-chlorophenyl)-16,17,18,19,20-pentanor-prostenoic acid,
(5Z)-(8R,11R,12R)-11-hydroxy-9-oxo-15,15-ethylenedioxy-17-phenyl-18,19,20-trinor-prostenoic acid,
(5Z)-(8R,11R,12R)-11-hydroxy-9-oxo-15,15-ethylenedioxy-16-(4-fluorophenoxy)-17,18,19,20-tetranor-prostenoic acid,
(5Z)-(8R,11R,12R)-11-hydroxy-9-oxo-15,15-ethylenedioxy-16-(4-chlorophenoxy)-17,18,19,20-tetranor-prostenoic acid,
(5Z)-(8R,11R,12R)-11-hydroxy-9-oxo-15,15-ethylenedioxy-16-(2-naphthyloxy)-17,18,19,20-tetranor-prostenoic acid,
(5Z,13E)-(8R,9S,12R)-9-hydroxy-11-oxo-15,15-ethylenedioxy-16-phenoxy-17,18,19,20-tetranor-prostadienoic acid,
(5Z,13E)-(8R,9S,12R)-9-hydroxy-11-oxo-15,15-ethylenedioxy-15-(4-chlorophenyl)-16,17,18,19,20-pentanor-prostadienoic acid,
(5Z,13E)-(8R,9S,12R)-9-hydroxy-11-oxo-15,15-ethylenedioxy-20-ethyl-prostadienoic acid,
(5Z,13E)-(8R,9S,12R)-9-hydroxy-11-oxo-15,15-ethylenedioxy-16-n-propoxy-17,18,19,20-tetranor-prostadienoic acid,
(5Z,13E)-(8R,9S,12R)-9-hydroxy-11-oxo-15,15-ethylenedioxy-19-oxa-prostadienoic acid,
(5Z,13E)-(8R,9S,12R)-9-hydroxy-11-oxo-15,15-ethylenedioxy-17-phenyl-18,19,20-trinor-prostadienoic acid,
(5Z,13E)-(8R,9S,12R)-9-hydroxy-11-oxo-15,15-ethylenedioxy-16-(4-fluorophenoxy)-17,18,19,20-tetranor-prostadienoic acid,
(5Z,13E)-(8R,9S,12R)-9-hydroxy-11-oxo-15,15-ethylenedioxy-16-(4-chlorophenoxy)-17,18,19,20-tetranor-prostadienoic acid,
(5Z,13E)-(8R,9S,12R)-9-hydroxy-11-oxo-15,15-ethylenedioxy-16-(2-naphthyloxy)-17,18,19,20-tetranor-prostadienoic acid,
(5Z,13E)-(8R,9S,12R)-9-hydroxy-11-oxo-15,15-ethylenedioxy-15-(1,3-dioxa-2-indanyl)-16,17,18,19,20-pentanor-prostadienoic acid,
(5Z,13E)-(8R,9S,12R)-9-hydroxy-11-oxo-15,15-ethylenedioxy-15-(4-biphenylyl)-16,17,18,19,20-pentanor-prostadienoic acid,
(5Z)-(8R,9S,12R)-9-hydroxy-11-oxo-15,15-ethylenedioxy-16-phenoxy-17,18,19,20-tetranor-prostenoic acid,
(5Z)-(8R,9S,12R)-9-hydroxy-11-oxo-15,15-ethylenedioxy-15-(4-chlorophenyl)-16,17,18,19,20-pentanor-prostenoic acid,
(5Z)-(8R,9S,12R)-9-hydroxy-11-oxo-15,15-ethylenedioxy-17-phenyl-18,19,20-trinor-prostenoic acid,
(5Z)-(8R,9S,12R)-9-hydroxy-11-oxo-15,15-ethylenedioxy-16-(4-fluorophenoxy)-17,18,19,20-tetranor-prostenoic acid,
(5Z)-(8R,9S,12R)-9-hydroxy-11-oxo-15,15-ethylenedioxy-16-(4-chlorophenoxy)-17,18,19,20-tetranor-prostenoic acid or
(5Z)-(8R,9S,12R)-9-hydroxy-11-oxo-15,15-ethylenedioxy-16-(2-naphthyloxy)-17,18,19,20-tetranor-prostenoic acid.

61. (13E)-(8R,9S,11R,12R)-9,11-Dihydroxy-15,15-ethylenedioxy-16-phenoxy-17,18,19,20-tetranor-prostenoic acid, a compound of claim 1.

62. (5Z,13E)-(8R,9R,11R12R)-9,11-Dihydroxy-15,15-ethylenedioxy-16-phenoxy-17,18,19,20-tetranor-prostadienoic acid, a compound of claim 1.

63. (5Z,13E)-(8R,9R,11R,12R)-9,11-Dihydroxy-15,15-ethylenedioxy-15-(4-chlorophenyl)-16,17,18,19,20-pentanor-prostadienoic acid, a compound of claim 1.

64. (5Z,13E)-(8R,9R,11R,12R)-9,11-Dihydroxy-15,15-ethylenedioxy-20-ethyl-prostadienoic acid, a compound of claim 1.

65. (5Z,13E)-(8R,9R,11R,12R)-9,11-Dihydroxy-15,15-ethylenedioxy-16-n-propoxy-17,18,19,20-tetranor-prostadienoic acid, a compound of claim 1.

66. (5Z,13E)-(8R,9R,11R,12R)-9,11-Dihydroxy-15,15-ethylenedioxy-19-oxa-prostadienoic acid, a compound of claim 1.

67. (5Z,13E)-(8R,9R,11R,12R)-9,11-Dihydroxy-15,15-ethylenedioxy-17-phenyl-18,19,20-trinor-prostadienoic acid, a compound of claim 1.

68. (5Z,13E)-(8R,9R,11R,12R)-9,11-Dihydroxy-15,15-ethylenedioxy-16-(4-fluorophenoxy)-17,18,19,20-tetranor-prostadienoic acid, a compound of claim 1.

69. (5Z,13E)-(8R,9R,11R,12R)-9,11-Dihydroxy-15,15-ethylenedioxy-16-(4-chlorophenoxy)-17,18,19,20-tetranor-prostadienoic acid, a compound of claim 1.

70. (5Z,13E)-(8R,9R,11R,12R)-9,11-Dihydroxy-15,15-ethylenedioxy-16-(2-naphthyloxy)-17,18,19,20-tetranor-prostadienoic acid, a compound of claim 1.

71. (5Z,13E)-(8R,9R,11R,12R)-9,11-Dihydroxy-15,15-ethylenedioxy-15-(1,3-dioxa-2-indanyl)-16,17,18,19,20-pentanor-prostadienoic acid, a compound of claim 1.

72. (5Z,13E)-(8R,9R,11R,12R)-9,11-Dihydroxy-15,15-ethylenedioxy-15-(4-biphenylyl)-16,17,18,19,20-pentanor-prostadienoic acid, a compound of claim 1.

73. (5Z)-(8R,9R,11R,12R)-9,11-Dihydroxy-15,15-ethylenedioxy-15-(4-chlorophenyl)-16,17,18,19,20-pentanor-prostenoic acid, a compound of claim 1.

74. (5Z)-(8R,9R,11R,12R)-9,11-Dihydroxy-15,15-ethylenedioxy-17-phenyl-18,19,20-trinor-prostenoic acid, a compound of claim 1.

75. (5Z)-(8R,9R,11R,12R)-9,11-Dihydroxy-15,15-ethylenedioxy-16-(4-fluorophenoxy)-17,18,19,20-tetranor-prostenoic acid, a compound of claim 1.

76. (5Z)-(8R,9R,11R,12R)-9,11-Dihydroxy-15,15-ethylenedioxy-16-(4-chlorophenoxy)-17,18,19,20-tetranor-prostenoic acid, a compound of claim 1.

77. (5Z)-(8R,9R,11R,12R)-9,11-Dihydroxy-15,15-ethylenedioxy-16-(2-naphthyloxy)-17,18,19,20-tetranor-prostenoic acid, a compound of claim 1.

78. (5Z)-(8R,9R,11R,12R)-9,11-Dihydroxy-15,15-ethylenedioxy-16-phenoxy-17,18,19,20-tetranor-prostenoic acid, a compound of claim 1.

79. (5Z,10Z,13E)-(8R,12R)-9-Oxo-15,15-ethylenedioxy-16-phenoxy-17,18,19,20-tetranor-prostatrienoic acid methyl ester, a compound of claim 1.

80. (5Z,10Z,13E)-(8R,12R)-9-Oxo-15,15-ethylenedioxy-15-(4-chlorophenyl)-16,17,18,19,20-pentanor-prostatrienoic acid methyl ester, a compound of claim 1.

81. (5Z,10Z,13E)-(8R,12R)-9-Oxo-15,15-ethylenedioxy-16-(4-fluorophenoxy)-17,18,19,20-tetranor-prostatrienoic acid methyl ester, a compound of claim 1.

82. (5Z,10Z,13E)-(8R,12R)-9-Oxo-15,15-ethylenedioxy-16-(4-chlorophenoxy)-17,18,19,20-tetranor-prostatrienoic acid methyl ester, a compound of claim 1.

83. (5Z,13E)-(8R,9S,11R,12R)-9,11-Dihydroxy-15,15-ethylenedioxy-15-(4-chlorophenyl)-16,17,18,19,20-pentanor-prostadienoic acid (4-biphenylyl) ester, a compound of claim 1.

84. (5Z,13E)-(8R,9S,11R,12R)-9,11-Dihydroxy-15,15-ethylenedioxy-20-ethyl-prostadienoic acid (4-biphenylyl) ester, a compound of claim 1.

85. (5Z,13E)-(8R,9S,11R,12R)-9,11-Dihydroxy-15,15-ethylenedioxy-16-(p-chlorophenyloxy)-17,18,19,20-tetranor-prostadienoic acid (4-biphenylyl)ester, a compound of claim 1.

86. (5Z,13E)-(8R,9S,11R,12R)-9,11-Dihydroxy-15,15-ethylenedioxy-16-(3-trifluoromethylphenyloxy)-17,18,19,20-tetranor-prostadienoic acid, a compound of claim 1.

87. (5Z,13E)-(8R,9S,11R,12R)-9,11-Dihydroxy-15,15-ethylenedioxy-16-(3-trifluoromethylphenyloxy)-17,18,19,20-tetranor-prostadienoic acid methyl ester, a compound of claim 1.

88. A pharmaceutical composition comprising in unit dosage form a compound of claim 1 in admixture with a pharmaceutically acceptable carrier.

89. A method of synchronization of the sexual cycle in female mammals which comprises administering to a fertile female mammal an amount of a compound of claim 1 in doses of 0.1 - 2 mg. effective to effect the synchronization of her sexual cycle.

90. A compound of the formula

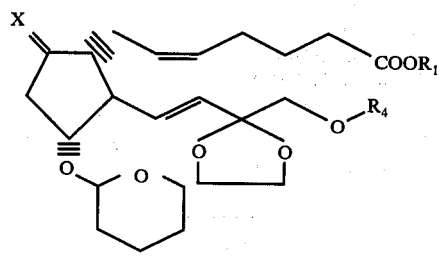

wherein X is =O or HOH, $R_1$ is a hydrogen atom, alkyl of 1-10 carbon atoms, unsubstituted aryl, aryl substituted by 1-3 halogen atoms, one phenyl group, 1-3 alkyl groups of respectively 1-4 carbon atoms or one chloromethyl, fluoromethyl, trifluoromethyl, carboxyl or hydroxy group, or —$CH_2$—U—V wherein U is a direct bond, carbonyl, or carbonyloxy and V is phenyl substituted by at least one of phenyl, alkoxy of 1-2 carbon atoms or a halogen atom and $R_4$ is alkyl of 1-10 carbon atoms, alkyl of 1-5 carbon atoms substituted by unsubstituted aryl or by aryl substituted by 1-3 halogen atoms, one phenyl group, 1-3 alkyl groups of respectively 1-4 carbon atoms or one chloromethyl, fluoromethyl, trifluoromethyl, carboxyl or hydroxy group, unsubstituted or substituted aryl or benzodioxol-2-yl.

* * * * *